(12) United States Patent
Huang et al.

(10) Patent No.: US 9,816,127 B2
(45) Date of Patent: Nov. 14, 2017

(54) OXIDIZED GLUTATHIONE ASSAY

(75) Inventors: Fen Huang, Madison, WI (US); Dieter Klaubert, Arroyo Grande, CA (US); John Shultz, Verona, WI (US); Wenhui Zhou, Santa Maria, CA (US)

(73) Assignee: PROMEGA CORPORATION, Madison, WI (US)

( * ) Notice: Subject to any disclaimer, the term of this patent is extended or adjusted under 35 U.S.C. 154(b) by 87 days.

(21) Appl. No.: 13/222,697

(22) Filed: Aug. 31, 2011

(65) Prior Publication Data

US 2012/0058501 A1 Mar. 8, 2012

Related U.S. Application Data

(60) Provisional application No. 61/379,203, filed on Sep. 1, 2010.

(51) Int. Cl.

| G01N 21/76 | (2006.01) |
|---|---|
| C12Q 1/66 | (2006.01) |
| C12Q 1/48 | (2006.01) |
| C12P 21/02 | (2006.01) |
| A61K 38/00 | (2006.01) |

(52) U.S. Cl.
CPC ............. *C12Q 1/48* (2013.01); *G01N 21/763* (2013.01); *G01N 2333/91177* (2013.01)

(58) Field of Classification Search
CPC ....... G01N 21/763; G01N 2333/91177; C12Q 1/66; C12Y 113/12007
See application file for complete search history.

(56) References Cited

U.S. PATENT DOCUMENTS

| 6,235,495 | B1 * | 5/2001 | Fu et al. .......................... 435/25 |
| 2002/0016284 | A1 * | 2/2002 | Perry et al. ....................... 514/1 |
| 2007/0015790 | A1 * | 1/2007 | Cali et al. ..................... 514/314 |

FOREIGN PATENT DOCUMENTS

| JP | 2008/545746 | 12/2008 |
| WO | WO 01/35097 | 5/2001 |
| WO | WO 02/103036 | 12/2002 |

OTHER PUBLICATIONS

"Promega (2008) "GSH-GLO Glutathione Assay, www.promega.com, pp. 1-20.*
Glatz et al. (1997) Use of thiopropyl Sepharose for the synthesis of an adsorbent for the affinity chromatography of glutathione S-transferase, J. Chromatog. B., vol. 688, pp. 239-243.*
Mistry et al. (1991) Evidence that rat liver pyruvate dehydrogenase kinase activator protein is a pyruvate dehydrogenase kinase, Biochem. J., vol. 275, pp. 775-779.*
Wendell P.L. (1970) Measurement of Oxidized Glutathione and Total Glutathione in the Perfused Rat Heart, Biochem. J., vol. 177, pp. 661-665.*
Hiranruengchok et al. (1995) Formation of Protein-Glutathione Mixed Disulfides in the Developing Rat Conceptus Following Diamide Treatment in Vitro, Teratology, vol. 52, pp. 196-204.*
Liu et al. (2005) Characterization of E3-histone, a novel testis ubiquintin protein ligase which ubiquitinates histones, Mol. Cell. Biol., Vo. 25, No. 7, pp. 2819-2831.*
PanReac AppliChem (2003) N-Ethylmaleimide BioChemica, https://www.applichem.com/en/shop/product-detail/as/n-ethylmaleimid-ibiochemicai, p. 1-2.*
Sigma (2009) Glutathione assay kit, pp. 1-4.*
Sigma-Aldrich (2009) Material Safety Data Sheet, p. 1.*
Walker, J. et al., "Biochemical properties of cloned glutathione S-transferases from Schistosoma mansoni and Schistosoma japonicum," Mol. Biochem. Parasitology (1993) 61:255-264.
Mourad, T. et al., "Measurement of oxidized glutathione by enzymatic recycling coupled to bioluminescent detection," Anal. Biochem. (2000) 283:146-152.
Winters, R.A. et al., "Analysis of glutathione, glutathione disulfide, cysteine, homocysteine, and other biological thiols by high-performance liquid chromatography following derivatization by N-(1-pyrenyl)maleimide," Anal. Biochem. (1995) 227:14-21.
Monostori, P. et al., "Determination of glutathione and glutathione disulfide in biological samples: an in-depth review," J. Chromat. B (2009) 877:3331-3346.
Ates, B. et al., "Determination of glutathione disulfide levels in biological samples using thiol-disulfide exchanging agent, dithiothreitol," Biomed. Chromat. (2009) 23(2):119-123.
Asensi, M. et al., "A high-performance liquid chromatography method for measurement of oxidized glutathione in biological samples," Anal. Biochem. (1994) 217(2):323-328.
International Search Report and Written Opinion for Application No. PCT/US2011/049964 dated Nov. 14, 2011 (14 pages).
Van Bladeren, Chemico-Biological Interactions. 129: 61-76 (2000).
Ploemen et al., "Irreversible Inhibition of Human Glutathione S-Transferase Isoenzymes Tetracloro-1, 4-Benzoquinone and its Glutathione Conjugate," Biochemical Pharmacology, 1991, vol. 4, No. 11, pp. 1665-1669.
Van Ommen et al., "Active Site-directed Irreversible Inhibition of Glutathione S-Transferases by the Glutathione Conjugate of Tetrachloro-1, 4-benzoquinone," The Journal of Biological Chemistry, 1988, vol. 263, No. 26, pp. 12939-12942.
Yasgar et al., "A High-Throughput 1,536-Well Luminescence Assay for Glutathione S-Transferase Activity," ASSAY and Drug Development Technologies, Apr. 2010, pp. 200-211.
Japanese Patent Office Action for Application No. 2013-527266 dated Aug. 17, 2015 (7 pages, including English translation).
Kamencic et al., "Monochlorobimane Fluorometric Method to Measure Tissue Glutathione," Analytical Biochemistry, 286, pp. 35-37 (2000).

* cited by examiner

*Primary Examiner* — Manjunath Rao
*Assistant Examiner* — Samuel Liu
(74) *Attorney, Agent, or Firm* — Michael Best & Friedrich LLP

(57) ABSTRACT

The present invention provides an assay for detection of oxidized glutathione (GSSG).

31 Claims, 14 Drawing Sheets

Table 3

| | 1 | 2 | 3 | 4 | 5 | 6 | 7 | 8 | 9 | 10 | 11 | 12 |
|---|---|---|---|---|---|---|---|---|---|---|---|---|
| A | 407013 | 1562981 | 2662059 | 3797493 | 4681227 | 5044798 | 890935 | 1308030 | 1753588 | 2059009 | 2467733 | 483726 |
| B | 442086 | 1591357 | 2815872 | 3530802 | 4343846 | 4984588 | 807351 | 1289672 | 1680073 | 1986602 | 2303591 | 458401 |
| C | 5268109 | 5728808 | 5946657 | 5503575 | 5846228 | 5535035 | 5725776 | 5946573 | 6074604 | 6221276 | 6565852 | 4937391 |
| D | 5241427 | 5369735 | 6398062 | 5458302 | 5633540 | 5808347 | 5357057 | 5789160 | 5507896 | 6034628 | 6627440 | 4969099 |
| E | 463972 | 4308209 | 519028 | 531845 | 570266 | 565987 | 922802 | 1388351 | 1746899 | 2067466 | 2428833 | 484713 |
| F | 685849 | 4062210 | 499671 | 511754 | 540192 | 570139 | 887208 | 1307690 | 1755235 | 2080520 | 2460273 | 479820 |
| G | 886060 | 1046084 | 1513849 | 1925737 | 2286535 | 2492240 | 1077336 | 1560849 | 1869075 | 2150122 | 2538949 | 650441 |
| H | 629759 | 1097890 | 1478478 | 1943248 | 2380593 | 2619726 | 1108238 | 1480035 | 1863498 | 2352220 | 2571938 | 588988 |

FIG. 4A

Table 4

| PLB No NEM Section Type | Wells | Concentration of Titrated Compound [μM] | | | | | |
|---|---|---|---|---|---|---|---|
| | | 0 | 5 | 10 | 15 | 20 | 25 |
| GSH Alone | A1-B6 | 424,835 | 1,587,269 | 2,638,866 | 3,664,048 | 4,462,437 | 5,014,693 |
| GSSG Alone | A7-B12 | 471,064 | 852,143 | 1,299,361 | 1,706,571 | 2,008,808 | 2,385,662 |
| GSSG in 25uM GSH #1 | C1-D6 | 5,249,768 | 5,543,278 | 5,672,360 | 5,506,469 | 5,739,884 | 5,673,693 |
| GSSG in 25uM GSH #2 | C7-D12 | 5,541,417 | 5,852,867 | 5,791,238 | 6,127,952 | 6,446,646 | 4,963,545 |

FIG. 4B

Table 5

| PLB With NEM | | Concentration Of Compound Added (μM) | | | | | |
|---|---|---|---|---|---|---|---|
| | Wells | 0 | 5 | 10 | 15 | 20 | 25 |
| GSH Alone | E1-F6 | 574,911 | 492,210 | 509,349 | 521,800 | 559,229 | 568,063 |
| GSSG Alone | E7-F12 | 482,167 | 905,888 | 1,337,121 | 1,750,367 | 2,073,997 | 2,444,553 |
| GSSG in 25uM GSH #1 | G1-H6 | 603,405 | 1,871,977 | 1,496,163 | 1,934,492 | 2,323,064 | 2,555,983 |
| GSSG in 25uM GSH #2 | G7-H12 | 619,715 | 1,892,787 | 1,515,342 | 1,866,267 | 2,293,121 | 2,555,444 |

FIG. 4C

OXIDIZED GLUTATHIONE ASSAY

CROSS-REFERENCE TO RELATED APPLICATIONS

This application claims the benefit of U.S. Application Ser. No. 61/379,203 which was filed Sep. 1, 2010.

SUMMARY OF THE INVENTION

The present invention provides an assay for detection of oxidized glutathione (GSSG) and the determination of the ratio of GSH and GSSG in a cell.

BACKGROUND OF THE INVENTION

To remain healthy, cells, in particular mammalian cells, need to maintain a balance between oxidizing and reducing conditions sometimes referred to as redox state/potential. One of the most important mechanisms used to set and preserve the redox state/potential occurs through maintaining the relative amounts of oxidized and reduced glutathione in the cell.

Glutathione is a peptide made from three amino acids: glutamic acid, cysteine and glycine. It is often present at a much higher concentration in the cell than other proteins and peptides. Glutathione can exist in multiple forms in a cell. The two forms most often considered to relate to the cell's redox state/potential are GSH and GSSG. GSH, the reduced form, occurs when glutathione is unbound to other molecules (Monostori et al. 2009. J. Chromatography B 877: 3331-3346). GSSG, the oxidized form, occurs when a disulfide bond exists between two glutathione molecules. GSH is often considered a first line of defense against oxidative damage and can remove active species from the cell and form GSSG. The presence of GSSG in plasma is often an indication of stress management. Since GSH and GSSG are related to each other through a simple oxidation/reduction reaction, they establish a redox state/potential within the cell. Further, since GSH and GSSG in total typically make up the highest redox couple in the cell, the determination of the amount of GSH and GSSG in a cell is usually performed, and the ratio of GSH to GSSG reported as a measure of the redox potential of the cell. Changes in the ratio of GSH and GSSG is often used as a measurement of oxidative damage in the cell.

Therefore, there exists a need to accurately and rapidly determine the ratio of GSH to GSSG in cells. Numerous reports indicate that compounds such as acetaminophen, tamoxifen, isoniazid and amodiaquine dramatically reduce the ratio of GSH to GSSG leading to cell death by apoptosis or necrosis (Srivastava et al. 2010. Handb. Exp. Pharmacol 196:165-94). Since variations in the ratio of GSH to GSSG have been reported to be associated with cell death, there is a need to be able to accurately determine this ratio (Monostori et al. 2009).

While multiple methods exist for the measurement of GSH in a sample, the most commonly used is the combination of an enzyme, such as glutathione reductase with Ellman's reagent (Monostori et al. 2009) and chromatographic methods, e.g. HPLC methods (Monostori et al. 2009). These methods utilize several processing steps including acidification, protein removal by precipitation, neutralization, internal control addition and others before sample addition for glutathione measurement (Monostori et al. 2009). As GSH is easily converted to GSSG, such as by exposure to air, preserving the initial amounts of GSSG and GSH in a sample for an accurate ratio measurement is difficult using techniques that require many processing steps. Therefore, these methods often require the addition of internal standards to allow estimations to be made of the amount of material lost and oxidized during the processing steps.

Measurement of the GSSG level in samples is even more difficult using the above methods. Since GSSG is typically only a small fraction of the GSH in the sample, relatively small changes in the amount of GSSG in a sample can result in dramatic changes in the GSH/GSSG ratio. For example, if the actual GSH/GSSG molar ratio is 100 (from a cellular concentration of GSH of 10 mM and GSSG of 100 µM), and the level of GSH drops from 10 to 9.8 mM (a 2% change) with an increase in GSSG of 100 µM [since two moles of GSH are needed to generate a mole of GSSG], the GSSG level changes from 100 µM to 200 µM [a 100% change], and the ratio of GSH to GSSG changes from 100 to 49 [a two fold change]. Thus, accurate measurement of the amount of GSSG in the sample is essential for correctly determining the GSH/GSSG ratio.

Several methods for determination of GSSG have been reported. A number of these methods calculate the level of GSSG in a sample by initially measuring the level of GSH and then measuring the level of GSH after reducing all of the GSSG to GSH (Monostori et al. 2009). The level of GSSG is then estimated by subtracting the amount of GSH found in the initial measurement of GSH from that of the level of GSH following reduction of GSSG to GSH. This results in the level of GSSG being determined by calculating the difference between two relatively large numbers, both of which have some degree of variability, and therefore, are highly error prone.

Other methods for the measurement of GSSG require that GSH first be chemically modified in the sample to prevent it from giving a signal in the GSH measurement reaction. Then, the GSSG in the sample is reduced to GSH and, finally, the resulting GSH generated from GSSG is measured. While such a method might be accurate in theory, there is a need to remove or inactivate the material used to mask the GSH before reducing the GSSG to GSH. If this is not done, the GSH formed will immediately be modified to the form generated by the blocking agent, resulting in an underestimate of the level of GSSG in the sample. In such cases, alkylating agents such as N-ethylmalamide (NEM) are used to rapidly and irreversibly modify the GSH into a form that will not give signal in the GSH measurement reaction. Unfortunately, these methods rely on the use of chemical reactions that give signal with any sulfhydryl reagent present in the sample. Thus, the alkylating reagent usually cannot be simply exhausted by addition of an excess of a sulfhydryl reagent that will exhaust the material. For this reason, these methods must remove all traces of excess reagent (such as NEM) resulting in the need to extract the solution—up to 9 times—greatly complicating sample processing and increasing the possibility of GSH loss.

Therefore, there is a need for a method to determine the amount of GSH, GSSG and/or the ratio of GSH to GSSG in an accurate and rapid manner, specifically a method is needed that requires few, if any, processing steps. The method of the present invention uses an enzymatic reaction for the measurement of the amount of GSH in a sample which requires no processing steps and prevents GSH loss.

BRIEF DESCRIPTION OF THE FIGURES

FIG. 4A-C shows fluorescent detection using luciferin derivatives.

DETAILED DESCRIPTION OF THE INVENTION

Figure 1:
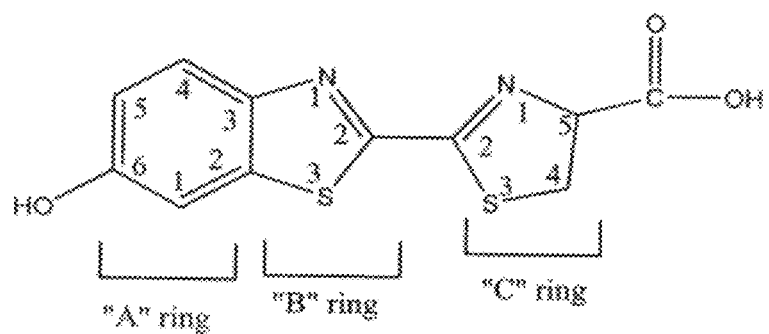
FIG. 1 shows the numbering of ring atoms in the six membered ring ("A ring" or "ring A"), five membered center ring ("B ring" or "ring B"), and other five membered ring ("C ring" or "ring C") of beetle luciferin (D-luciferin).

The method of the invention uses an enzymatic reaction for the measurement of the amount of GSSG in a sample. The method of the present invention comprises contacting a sample, for example one which contains cell(s), with a lysing agent and a modifying agent, e.g. sulfhydryl alkylating agent such as N-ethylmaleimide (NEM). The sample, e.g., a lysed cell(s) is then contacted with a substrate, glutathione-S-transferase (GST) and an excess of a reducing agent, and a signal generated by the interaction of GST with the substrate is detected. The particular enzymatic reaction used is specific for reduced glutathione (GSH) and does not give a signal from other sulfhydryls that may be present in a sample. The specificity of the enzymatic reaction allows the elimination of the active alkylating reagent (e.g. NEM) by greatly overwhelming the alkylating reagent through the addition of a sulfhydryl reducing reagent, e.g. DTT, in far excess of the alkylating agent. The addition also has the added advantage of reducing any GSSG in the sample to GSH, inactivating the excess alkylating agent and reducing the GSSG to GSH, and eliminating the need for separate steps for each of these manipulations. In addition, since the reaction of the alkylating agent (e.g. NEM) with the reducing agent is essentially instantaneous at the concentrations used in the method of the present invention (and the reducing agent does not give signal by itself or in combination with the alkylating reagent used with or without the enzyme present), the reducing agent can simply be added to the GSH detection reaction, thereby eliminating a separate step for GSH detection. Further, the reducing agents do not create a species which gives a luminescent signal with the pre-luciferin when added with the other reaction components. Thus, the method of the present invention can be used for the measurement of the level of GSSG in a sample by adding an amount of the alkylating agent (e.g. NEM) such that it is in excess of the amount of sulfhydryl moieties present in the sample, adding an amount of sulfhydryl reducing agent (such as DTT) to insure that any excess alkylating agent is immediately inactivated and any GSSG in the sample is reduced to GSH, and adding a GSH detection agent to detect the level of GSSG.

Another advantage of the method of the present invention is that the method only generates a signal specific to GSH, i.e., the method does not give signal from all the —SH groups in a sample [such as those that generate signal with Ellman's reagent or chemical detection reagents such as bromobimane (Clin. Chem. 1988. vol. 44, pp. 825-832 and Biochem J. 2006. vol 393, pp. 575-582)], therefore, there is no need to remove protein from the samples, e.g., by protein denaturation due to acidification of the sample followed by the removal of the precipitated protein by centrifugation.

By combining the above-mentioned features, the method of the present invention allows the accurate and rapid measurement of very low levels of oxidized glutathione in cellular extracts, cell media, or other biological sample, e.g., physiological fluid such as plasma, serum, blood, etc., and without the need for protein precipitation or excessive sample processing. The combination of the steps in the present invention, while very unpredictable, relies on many factors performing as needed for the method to be successful. For example:

1. The reagents used for signal generation from reduced glutathione must not generate substantial signal from other SH groups present in the sample, and;

2. The specificity of the GSH detection reaction will also not generate signal from the presence of other SH groups present in the reaction, including those present on proteins present in the sample, and;

3. The reaction of the alkylating agent with all SH groups present in the sample must be essentially immediate and complete within a very short period of time, thus allowing complete elimination of pre-existing GSH in the sample as soon as the reagent can access the GSH, and;

4. The agent used to release GSH from the cell must not inactivate the alkylating reagent, yet it must rapidly and completely be able to lyse the cell, thus allowing for the complete elimination of GSH from the sample as soon as the reagent is added, thereby preventing the oxidation of any GSH in the sample to GSSG thus essentially "freezing" the level of GSSG in the sample, and;

5. The addition of the reducing agent added must first inactivate the alkylating agent before it can modify any GSH the reducing agent might form from GSSG in the sample or inactivating the GSH detecting enzyme (GST in this case), and;

6. The sensitivity of the luciferase-based detection system must be able to accurately detect very low levels of luciferin generated from the amount of GSSG present in a sample.

Therefore, the combination of all these factors to solve a problem that has existed for many years is both novel and unexpected.

Definitions

As used herein, the following terms and expressions have the indicated meanings. It will be appreciated that the compounds of the present invention contain asymmetrically substituted carbon atoms, and may be isolated in optically active or racemic forms. It is well known in the art how to prepare optically active forms, such as by resolution of racemic forms or by synthesis from optically active starting materials. All chiral, diastereomeric, racemic forms and all geometric isomeric forms of a structure are part of this invention.

Specific values listed below for radicals, substituents, and ranges, are for illustration only; they do not exclude other defined values or other values within defined ranges for the radicals and substituents.

As used herein, the term "substituted" is intended to indicate that one or more (e.g., 1, 2, 3, 4, or 5; in some embodiments 1, 2, or 3; and in other embodiments 1 or 2) hydrogens on the group indicated in the expression using "substituted" is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxylamine, hydroxyl(alkyl)amine, and cyano. Additionally, the suitable indicated groups can include, e.g., —X, —R, —O⁻, —OR, —SR, —S⁻, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR, —S(=O)$_2$O⁻, —S(=O)$_2$OH, —S(=O)$_2$R, —OS(=O)$_2$OR, —S(=O)$_2$NR, —S(=O)R, —OP(=O)O$_2$RR, —P(=O)O$_2$RR, —P(=O)(O)$_2$, —P(=O)(OH)$_2$, —C(=O)R, —C(=O)X, —C(S)R, —C(O)OR, —C(O)O, —C(S)OR, —C(O)SR, —C(S)SR, —C(O)NRR, —C(S) NRR, —C(NR)NRR, where each X is independently a halogen ("halo"): F, Cl, Br, or I; and each R is independently H, alkyl, aryl, heteroaryl, heterocycle, a protecting group or prodrug moiety. As would be readily understood by one skilled in the art, when a substituent is oxo (=O) or thioxo (=S), or the like, then two hydrogen atoms on the substituted atom are replaced.

As used herein, the term "alkyl" refers to a branched, unbranched, or cyclic hydrocarbon having, for example, from 1 to 30 carbon atoms, and often 1 to 12, or 1 to about 6 carbon atoms. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., alkylene).

The term "alkenyl" refers to a monoradical branched or unbranched partially unsaturated hydrocarbon chain (i.e. a carbon-carbon, sp$^2$ double bond). In one embodiment, an alkenyl group can have from 2 to 10 carbon atoms, or 2 to 6 carbon atoms. In another embodiment, the alkenyl group has from 2 to 4 carbon atoms. Examples include, but are not limited to, ethylene or vinyl, allyl, cyclopentenyl, 5-hexenyl, and the like. The alkenyl can be unsubstituted or substituted.

The term "alkynyl" refers to a monoradical branched or unbranched hydrocarbon chain, having a point of complete unsaturation (i.e. a carbon-carbon, sp triple bond). In one embodiment, the alkynyl group can have from 2 to 10 carbon atoms, or 2 to 6 carbon atoms. In another embodiment, the alkynyl group can have from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, 1-octynyl, and the like. The alkynyl can be unsubstituted or substituted.

The term "cycloalkyl" refers to cyclic alkyl groups of from 3 to 10 carbon atoms having a single cyclic ring or multiple condensed rings. The cycloalkyl ring can have 3 to 7 carbon atoms or 5 to 6 carbon atoms. Such cycloalkyl groups include, by way of example, single ring structures such as cyclopropyl, cyclobutyl, cyclopentyl, cyclooctyl, and the like, or multiple ring structures such as adamantanyl, and the like. The cycloalkyl can be unsubstituted or substituted. The cycloalkyl group can be monovalent or divalent, and can be optionally substituted as described above for alkyl groups. The cycloalkyl group can optionally include one or more cites of unsaturation, for example, the cycloalkyl group can include one or more carbon-carbon double bonds, such as, for example, cyclohexene, 1,3-cyclohexadiene, 1,4-cyclohexadiene, and the like.

The term "alkoxy" refers to the group alkyl-O—, where alkyl is as defined herein. In one embodiment, alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

As used herein, "aryl" or "Ar" refers to an aromatic hydrocarbon group derived from the removal of one hydrogen atom from a single carbon atom of a parent aromatic ring system. The radical can be at a saturated or unsaturated carbon atom of the parent ring system. The aryl group can have from 6 to 30 carbon atoms. In other embodiments, an aryl group can have from 6 to 12 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups.

The term "halo" refers to fluoro, chloro, bromo, and iodo. Similarly, the term "halogen" refers to fluorine, chlorine, bromine, and iodine.

The term "haloalkyl" refers to alkyl as defined herein substituted by 1 or more halo groups as defined herein, which may be the same or different. In one embodiment, the haloalkyl can be substituted with 1, 2, 3, 4, or 5 halo groups. In another embodiment, the haloalkyl can by substituted with 1, 2, or 3 halo groups. The term haloalkyl also include perfluoro-alkyl groups. Representative haloalkyl groups include, by way of example, trifluoromethyl, 3-fluorododecyl, 12,12,12-trifluorododecyl, 2-bromooctyl, 3-bromo-6-chloroheptyl, 1H,1H-perfluorooctyl, and the like. The haloalkyl can be optionally substituted as described above for alkyl groups.

The term "heteroaryl" is defined herein as a monocyclic, bicyclic, or tricyclic ring system containing one, two, or three aromatic rings and containing at least one nitrogen, oxygen, or sulfur atom in an aromatic ring, and that can be unsubstituted or substituted, for example, with one or more, and in particular one to three, substituents, as described above in the definition of "substituted". Typical heteroaryl groups contain 2-20 carbon atoms in addition to the one or more hetoeroatoms. In other embodiments, a heteroaryl group may contain from 3 to 15 carbon atoms in addition to the one or more heteroatoms or 4 to 10 carbon atoms in addition to the one or more heteroatoms. In certain embodiments, the heteroaryl ring contains a total of 5 to 12 ring atoms including both carbon and heteroatoms or 5 to 10 ring atoms or 5 to 7 ring atoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl.

In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or ($C_1$-$C_6$) alkylaryl. In another embodiment heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, and sulfur, and optionally substituted with one or more groups as defined herein under the term "substituted". A heterocycle can be a monocyclic, bicyclic, or tricyclic group containing one or more heteroatoms. In some embodiments, the heterocycle contains a total of 3 to 20 ring atoms or a total of 5 to 20 ring atoms or 5 to 12 ring atoms. In certain embodiments, a heterocycle includes 1 to 4 heteroatoms or one, two, three or four heteroatoms. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The term "heterocycle" can include, by way of example and not limitation, a monoradical of the heterocycles described in Paquette, Leo A.; *Principles of Modern Heterocyclic Chemistry* (W.A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* 1960, 82, 5566. In one embodiment, "heterocycle" includes a "carbocycle" as defined herein, wherein one or more (e.g. 1, 2, 3, or 4) carbon atoms have been replaced with a heteroatom (e.g. O, N, or S).

Examples of heterocycles, by way of example and not limitation, include, dihydroypyridyl, tetrahydropyridyl(piperidyl), thiazolyl, tetrahydrothiophenyl, sulfur oxidized tetrahydrothiophenyl, pyrimidinyl, furanyl, thienyl, pyrrolyl, pyrazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, and the like.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. In one embodiment, nitrogen bonded heterocycles include 1-aziridyl, 1-azetedyl, 1-pyrrolyl, 1-imidazolyl, 1-pyrazolyl, and 1-piperidinyl.

The term "carbocycle" refers to a saturated, unsaturated or aromatic ring having 3 to 8 carbon atoms as a monocycle, 7 to 12 carbon atoms as a bicycle, and up to about 30 carbon atoms as a polycycle. Monocyclic carbocycles typically have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo[5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. The carbocycle can be optionally substituted as described above for alkyl groups.

The term "alkanoyl" or "alkylcarbonyl" refers to —C(=O)R, wherein R is an alkyl group as previously defined.

The term "acyloxy" or "alkylcarboxy" refers to —O—C(=O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

The term "alkoxycarbonyl" refers to —C(=O)OR (or "COOR"), wherein R is an alkyl group as previously defined.

The term "amino" refers to —$NH_2$. The amino group can be optionally substituted as defined herein for the term "substituted".

The term "alkylamino" refers to —$NR_2$, wherein at least one R is alkyl and the second R is alkyl or hydrogen. The term "acylamino" refers to N(R)C(=O)R, wherein each R is independently hydrogen, alkyl, or aryl.

The term "interrupted" indicates that another group is inserted between two adjacent carbon atoms (and the hydrogen atoms to which they are attached (e.g., methyl ($CH_3$), methylene (CH$_2$) or methine (CH))) of a particular carbon chain being referred to in the expression using the term "interrupted," provided that each of the indicated atoms' normal valency is not exceeded, and that the interruption results in a stable compound. Suitable groups that can interrupt a carbon chain include, e.g., with one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) and sulfonyl (SO$_2$). Alkyl groups can be interrupted by one or more (e.g., 1, 2, 3, 4, 5, or about 6) of the aforementioned suitable groups. The site of interruption can also be between a carbon atom of an alkyl group and a carbon atom to which the alkyl group is attached.

The term "luciferase," unless specified otherwise, refers to a naturally occurring, recombinant or mutant luciferase. The luciferase, if naturally occurring, may be obtained easily by the skilled person from an organism. If the luciferase is one that occurs naturally or is a recombinant or mutant luciferase, i.e., one which retains activity in a luciferase-luciferin reaction of a naturally occurring luciferase, it can be obtained readily from a culture of bacteria, yeast, mammalian cells, insect cells, plant cells, or the like, transformed to express a nucleic acid encoding the luciferase. Further, the recombinant or mutant luciferase can be derived from an in vitro cell-free system using a nucleic acid encoding the luciferase. Luciferases are available from Promega Corporation, Madison, Wis.

As used herein, a "fluorophore" includes a molecule which is capable of absorbing energy at a wavelength range and releasing energy at a wavelength range other than the absorbance range. Suitable, fluorophores include coumarin, fluorescein, rhodamines or any suitable xanthene dye, resorufin, or cresyl violet. The term "excitation wavelength" refers to the range of wavelengths at which a fluorophore absorbs energy. The term "emission wavelength" refers to the range of wavelengths that the fluorophore releases energy or fluoresces.

As used herein, a "bioluminogenic assay" or "bioluminogenic reaction" or "luminogenic assay" or "luminogenic reaction" includes a reaction in which a product of a reaction between a nonluciferase enzyme and a derivative of luciferin, aminoluciferin, or coelenterazine is a substrate for a luciferase or a product of a nonenzymatic reaction having a derivative of luciferin, aminoluciferin or coelenterazine is a substrate for a luciferase, or a reaction between a luciferase and a derivative of luciferin, aminoluciferin, or coelenterazine is bioluminogenic, i.e., produces a measurable amount of light.

As used herein, "bioluminescence" or "luminescence" is light produced as a result of a reaction between an enzyme and a substrate that generates light. Examples of such enzymes (bioluminescent enzymes) include firefly luciferase, e.g. *Photinus pyralis* or *Photinus pennslyvanica*, click beetle luciferase, *Renilla* luciferase, cypridina luciferase, *Oplophorus* luciferase, e.g. *Oplophorous gracilirostris, Aequorin photoprotein*, obelin photoprotein and the like.

A "luciferase reaction mixture" contains a luciferase enzyme and materials that will allow the luciferase enzyme to generate a light signal. The materials needed, and the particular concentrations and/or amounts, of the materials needed to generate a luminescent signal will vary depending on the luciferase enzyme used as well as the type of luciferase-based assay being performed. In general, for firefly luciferase, these materials can include: ATP, a magnesium salt, such as magnesium chloride, a firefly luciferase enzyme and a luciferin capable of generating light when the luciferin is used as a substrate for the firefly luciferase. Often other materials will be added to the solution including: a buffer to maintain the reaction at the proper pH, an additive such as PRIONEX or Bovine serum albumin (BSA) to help maintain luciferase activity, reducing agents, detergents, etc.

As used herein a "derivative of luciferin" or a "derivative of aminoluciferin" is a molecule that is a substrate for a nonluciferase enzyme, e.g. GST, and a prosubstrate of a luciferase, or a substrate for a nonluciferase enzyme, e.g. GST, and a substrate for a luciferase. The derivatives of the invention have one or more modifications to one or more of the three rings and/or substituents attached to one or more of the rings of the D-luciferin or aminoluciferin backbone (see FIG. 1).

A "fluorogenic assay" or "fluorogenic reaction" includes a reaction in which a product of a reaction between a nonluciferase, nonproteolytic enzyme, such as GST and a derivative of a fluorophore is fluorescent.

A "signal-generating moiety" or "reporter moiety" includes a fluorophore or a substrate for a luciferase, e.g., luciferin, aminoluciferin, or coelenterazine, or a chemiluminescent moiety, e.g. adamantyl 1,2-dioxetane.

Methods of Use

In one aspect, the invention provides a method of detecting GSSG in a sample. In another aspect, the invention provides a method of detecting the ratio of GSH to GSSG in a sample. Since the ratio of GSH to GSSG is often used to monitor the redox condition of a cell, the method of the present invention can be used to detect redox conditions in cells.

Generally, the method of the present invention comprises contacting a sample with a lysing agent and a modifying agent. For example, the sample may comprise a lysed cell which is then contacted with a substrate, glutathione-S-transferase (GST) and an excess of a reducing agent, and a signal generated by the interaction of GST with the substrate is detected. In certain embodiments, the signal is luminescence. In other embodiments, the signal is fluorescence. If the substrate is a substrate for luciferase, e.g., luciferin or a derivative of luciferin, a luciferase reaction mixture is added, and luminescence is detected. Alternatively, if the substrate comprises a reporter moiety, e.g. a fluorophore, it is detected using appropriate means known to those skilled in the art.

The reagents may be added sequentially or simultaneously. For example, the lysing agent and the sulfhydryl modifying agent may be added sequentially or simultaneously. If the reagents are added simultaneously, they may be in a single solution or multiple solutions.

The signal may be quantified if desired. The signal may be compared to a standard curve. The intensity of the signal is a function of the presence or amount of GSSG or GSH in the sample.

Suitable lysing agents include standard lysing buffers. For animal cells, a buffer with 0.1-1.0% non-ionic detergents, such as Triton X-100 or Tergitol, or ionic detergents, e.g., DTAB, is typically sufficient. Bacteria, plant, fungal or yeast cells are usually more difficult to lyse. Detergents, freeze/thaw cycles, hypotonic buffers, sonication, cavitation or combinations of these methods may be used.

Suitable sulfhydryl modifying agents include alkylating agents such as N-ethylmaleimide (NEM), 4 vinylpyridine (4-VP), and iodoacidamide. The amount of the sulfhydryl reagent typically used in the method of the invention should be approximately 2-10 fold higher than the expected level of reduced glutathione in the sample. For example, for treatment of approximately 1,000 to 20,000 cultured mammalian cells in a 96-well plate, a concentration of 50 µl of a 50-250 µM NEM solution is needed.

Suitable reducing agents are those with sulfhydryl groups such as dithiothreitol (DTT), 2-mercaptoethanol, cysteine, and cysteinamine. The amount of sulfhydryl reagent typically used in the method of the invention should be approximately 2-5 fold higher than the concentration of the alkylating agent added to the sample. For example, for processing of wells of mammalian cells in a 96-well cell culture plate, 50 µl of a 100-1,250 µM DTT solution is needed.

It should be kept in mind that not all alkylating or reducing agents are highly stable in aqueous solutions. For example, NEM can hydrolyze to produce a product that does not alkylate sulfhydryl groups. Thus, best results are achieved if the reagents are made just prior to use.

Suitable sources of glutathione-S-transferase (GST) include enzyme preparations that are essentially free of glutathione, e.g., Promega's glutathione-S-transferase (GST) enzyme (Cat. No. V687). It is very important to use a GST enzyme preparation that is essentially free of glutathione when performing the method of the present invention. Suitably, this means that there is less than 1 mole of GSH per mole of GST subunit. Many sources of GST enzyme contain high levels of glutathione as a result of the purification techniques used to produce the enzyme. Such preparations often contain sufficient glutathione to give unacceptably high background values when used to measure the levels of glutathione released from modest numbers of mammalian cells. In the method of the present invention, GST needs to be added in a sufficient amount to effectively generate a signal from the glutathione present in the sample. For example, for a 100 µl reaction, addition of about 1 to 10 µg of GST enzyme, more preferably 2-4 µg of enzyme, is needed to generate a signal.

The present invention may be used to determine the presence or amount of GSSG in any cells, e.g., cells cultured in a laboratory or cells obtained from an animal. Cells obtained from an animal may be tissue, tissue extracts, tissue lysates or homogenates, or the like. Cells may be eukaryotic cells, e.g., yeast, avian, plant, insect or mammalian cells, including but not limited to human, simian, murine, canine, bovine, equine, feline, ovine, caprine or swine cells, or prokaryotic cells, or cells from two or more different organisms, or cell lysates or supernatants thereof. The cells may have been genetically modified via recombinant techniques. In certain aspects, the cell may be in an animal, e.g., transgenic animals, or physiological fluid, e.g., blood, plasma, urine, mucous secretions or the like. In one embodiment, the methods of the present invention may be performed in vitro. In another embodiment, the methods of the present invention may be performed in vivo.

In addition, for any of the bioluminogenic assays described herein, other reagents may be added to reaction mixtures, including but not limited to those that inhibit or prevent inactivation of luciferase, or otherwise extend or enhance luminescent signal.

The substrate comprises a substrate for a nonluciferase enzyme, e.g. GST, which is a prosubstrate for a luciferase or is linked to a reporter moiety. The reporter moiety may be a fluorescent moiety e.g. coumarin and fluorescein, a chemiluminescent moiety, or a moiety that produces a color that can be detected via visual means or via its absorbance.

Substrates

Suitable substrates include, but are not limited to, compounds of Formulas (I), (II) and (III), below.

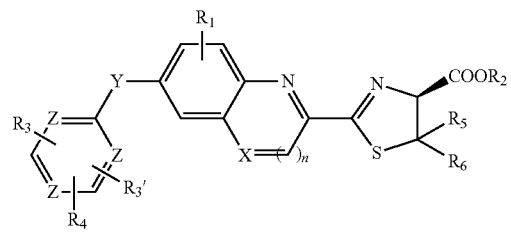
(I)

wherein n is 0 and X is S or n is 1 and X is CH;

wherein Y is O, $OSO_2$ or $OP(O)OR$, where R is any alkyl or aryl ester;

wherein $R_1$ is H, F, or OH;

wherein $R_2$ is H, alkyl, aryl, $CH_2Ar$, or $CH_2CH_2OH$;

wherein $R_3$, $R_3'$, $R_4$ are independently $NO_2$, $CF_3$, or H;

wherein Z is CH or N.

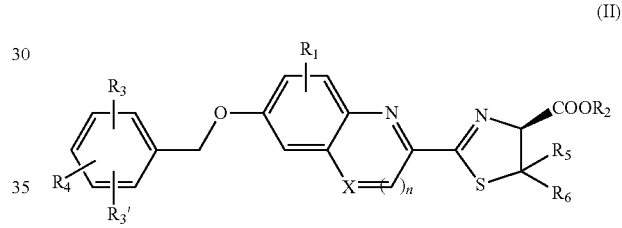
(II)

wherein n is 0 and X is S or n is 1 and X is CH;

wherein $R_1$ is H, F, or OH;

wherein $R_2$ is H, alkyl, aryl, $CH_2Ar$, or $CH_2CH_2OH$;

wherein $R_3$, $R_3'$, or $R_4$ are independently $NO_2$, $CF_3$, or H.

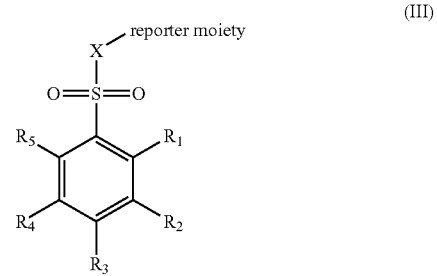
(III)

wherein X is N or O;

wherein $R_1$, $R_2$, $R_3$, $R_4$ and $R_5$ are independently H, lower alkyl ($C_1$-$C_6$), $CF_3$, halogen, $NO_2$, $CO_2R$ (where R is H or $C_{1-6}$ alkyl) or any two adjacent $R_1$-$R_5$ can form a fused ring (e.g., benzo, naphtho, hetrocyclic) provided that at least one of $R_1$, $R_3$ or $R_5$ is $NO_2$ and not all three are $NO_2$.

Figure 2A:
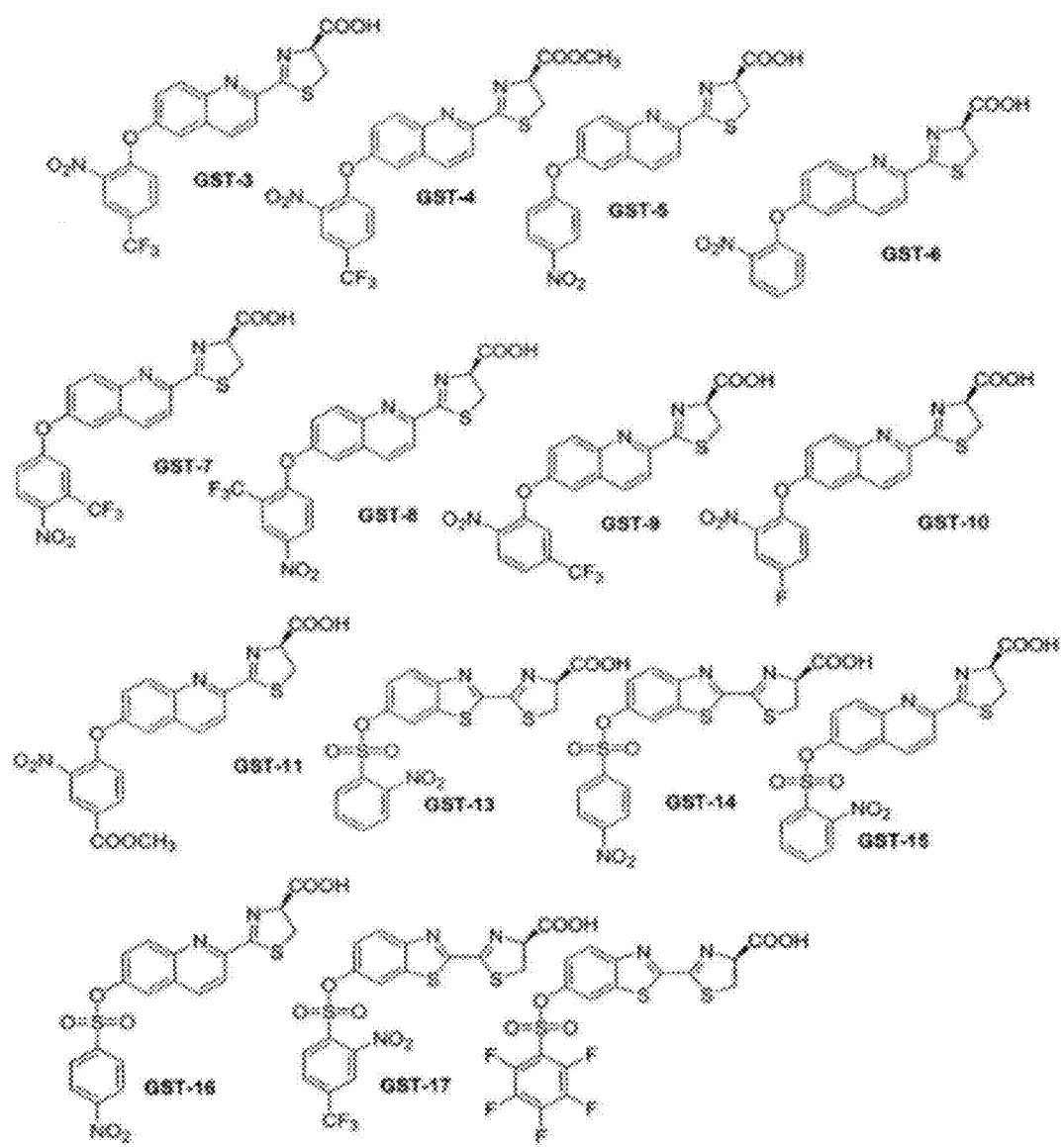
FIGS. 2A-B shows exemplary luciferin derivatives useful as substrates of glutathione-S-transferase (GST).
Figure 2B:
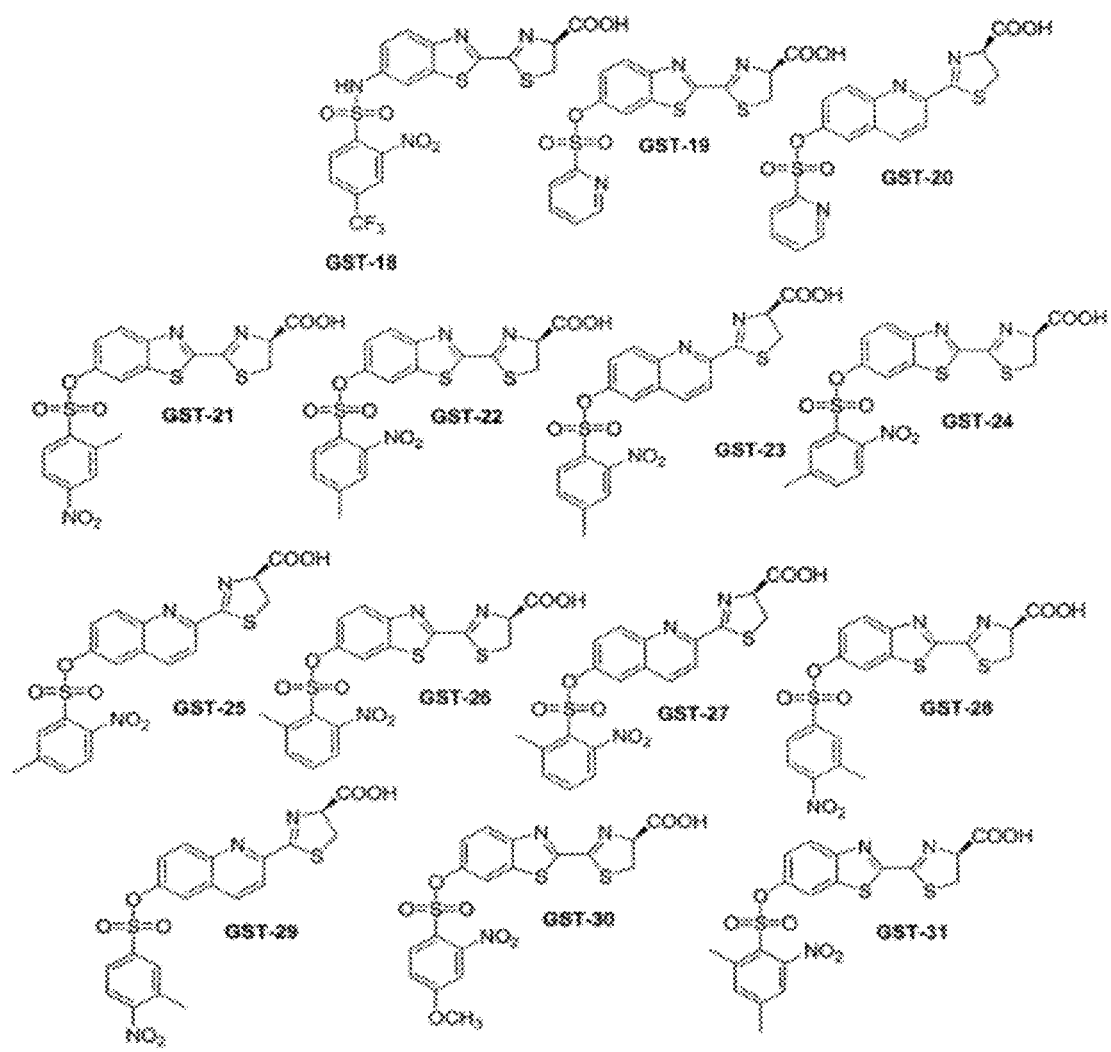
Figure 3:
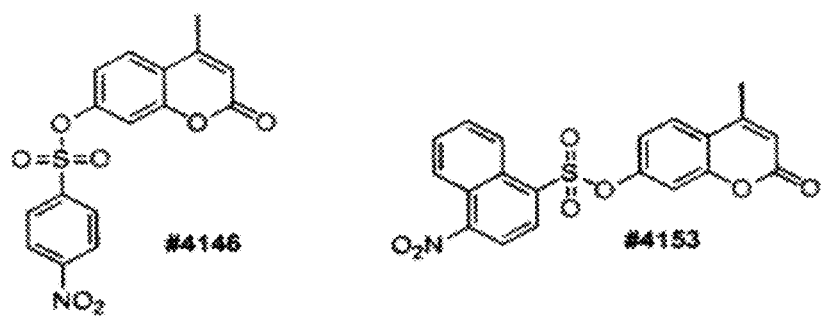
FIG. 3. shows exemplary fluorescent compounds useful as substrates of GST.
Figure 5A:
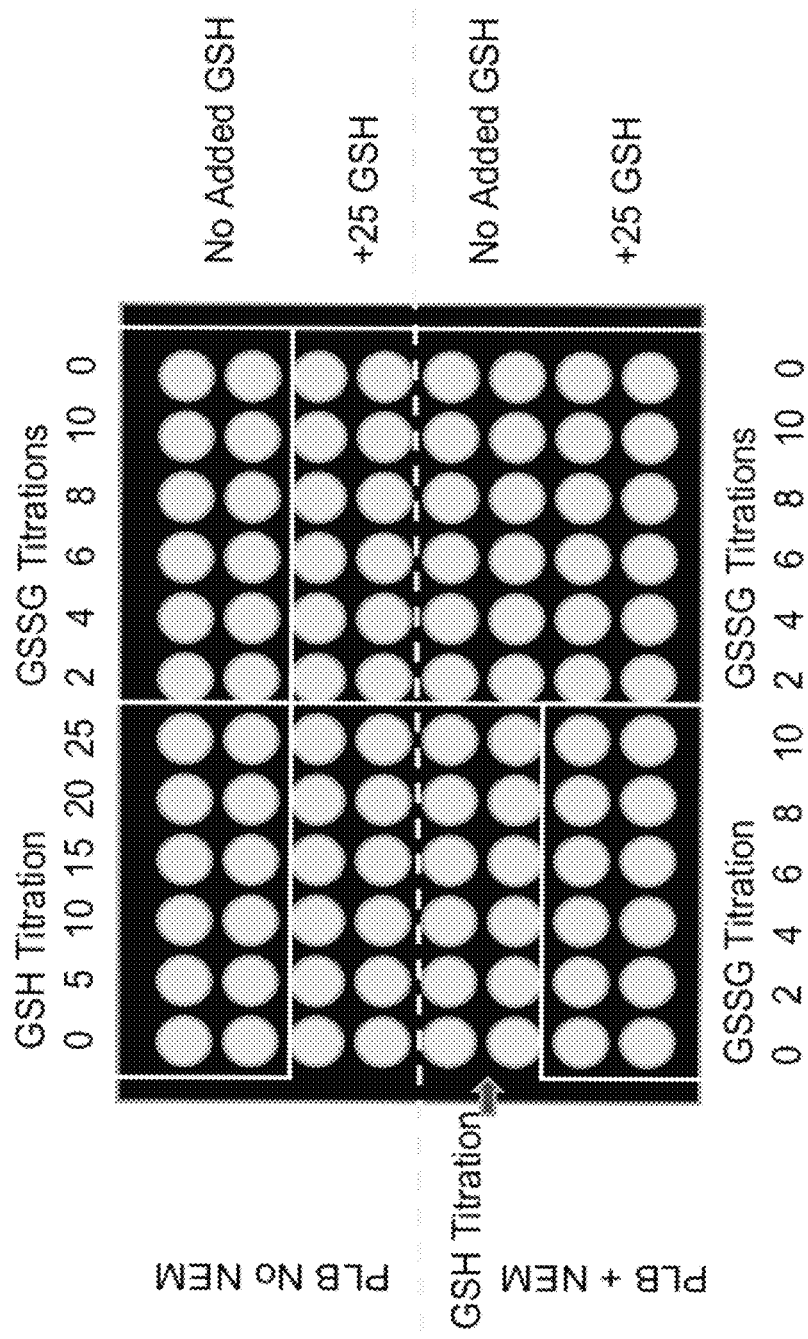
FIG. 5A-B shows fluorescent detection using luciferin derivatives.
Figure 5B:
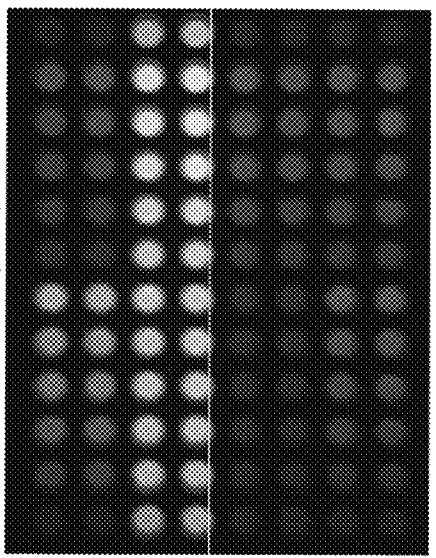
Figure 5B:
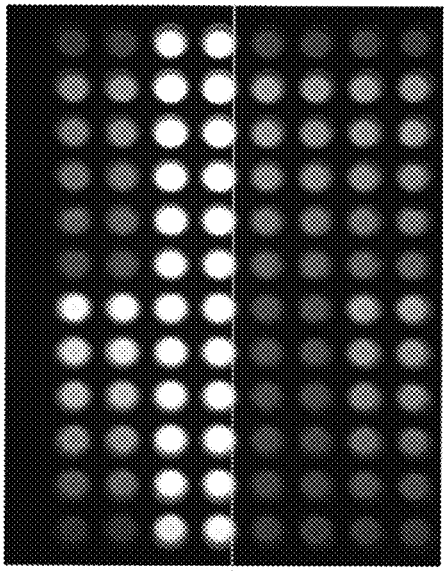
Figure 5B:
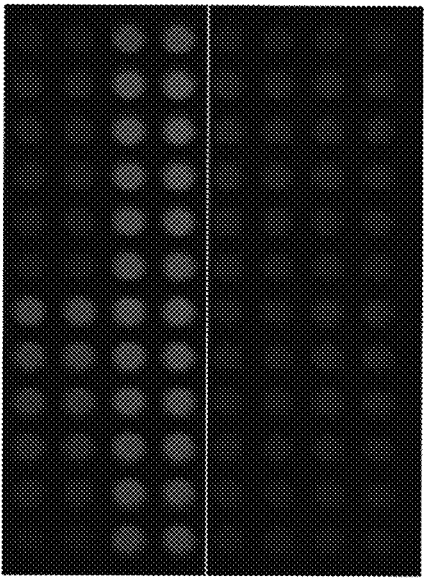
Figure 5B:
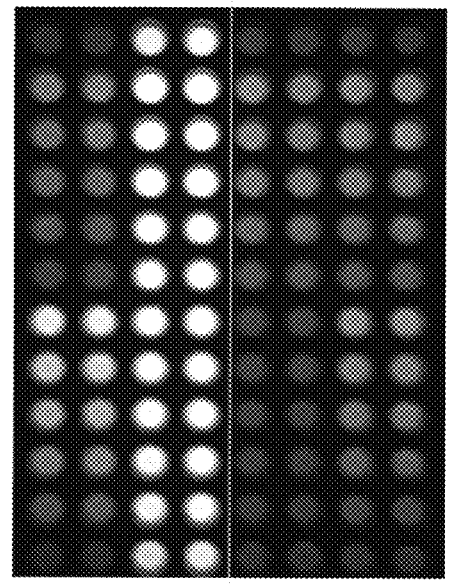

Additional substrates are shown in FIGS. 2 A-D and 3.

The invention is further described by the following non-limiting examples.

EXAMPLES

Example 1. Synthesis of 6-(2 nitro-4-trifluoromethyl-phenoxy)quinolinyl-luciferin (GST-3)

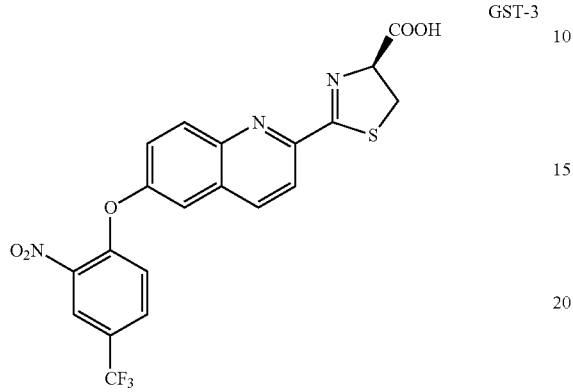

GST-3

Synthesis of 2-cyano-6-(2-nitro-4-trifluoromethyl-phenoxy)quinoline

A mixture of 2-cyano-6-hydroxyquinoline (0.50 g, 2.94 mmol), 2-nitro-4-trifluoromethylbenzene chloride (0.67 g, 2.94 mmol) and potassium carbonate (0.41 g, 2.97 mmol) in 30 ml of DMSO was heated to 100° C. for 30 min. Upon cooling to room temperature, the mixture was poured into 30 ml of cold water and extracted three times with methylene chloride. The combined organic layer was washed with water and dried over magnesium sulfate. The product was purified by flash chromatography using heptane/methylene chloride (1:2) as eluent in a yield of 35%. $^1$H NMR (CD$_2$Cl$_2$): 8.36 (d, 1H), 8.25 (dd, 1H), 7.94 (dd, 1H), 7.75 (d, 1H), 7.67 (dd, 1H), 7.43 (d, 1H), 7.31 (d, 1H). MS (ES) m/e (M+2): 361.

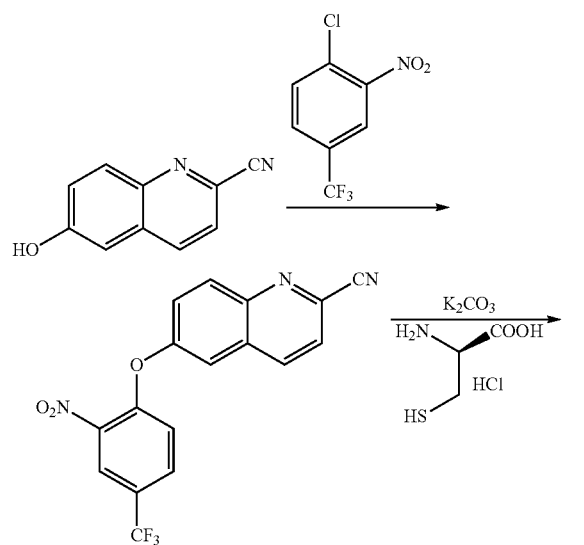

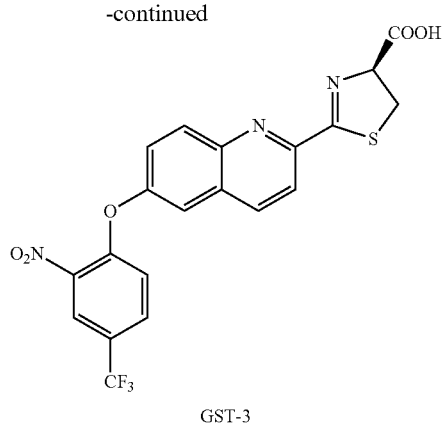

GST-3

Synthesis of GST-3

To a homogenous solution of 6-(2-nitro-4-(trifluoromethyl)phenoxy)-2-cyano-quinoline (1.079 g, 3.0 mmol) and D-cysteine (0.53 g, 3.0 mmol) in MeOH/CH$_2$Cl$_2$/water, a sufficient amount of K$_2$CO$_3$ to adjust pH to 7.5-8 was added. The mixture was stirred for 30 minutes until TLC indicated the starting material was completely consumed. The pH of the solution was then adjusted to 4-5 with acetic acid, extracted three times with CH$_2$Cl$_2$, and the organic layer dried over Na$_2$SO$_4$. After removal of the solvent, the compound was purified by flash chromatography using methylene chloride/methanol (95:5) as eluent in a yield of 20%. $^1$H NMR (d$_6$-DMSO): 8.55 (s, 1H), 8.42 (d, 1H), 8.19 (m, 2H), 8.06 (d, 1H), 7.82 (s, 1H), 7.71 (d, 1H), 7.46 (d, 1H), 5.22 (t, 1H, CHCOO), 3.45-3.75 (m, 2H, CH$_2$). MS (ES) m/e (M+1): 464. $\lambda_{max}$ 328 nm, $\epsilon_{max}$ 9,900 cm$^{-1}$M$^{-1}$ in MeOH.

Example 2. Synthesis of Methyl 6-(2-nitro-4-trifluoromethyl-phenoxy)quinolinyl-luciferin ester (GST-4)

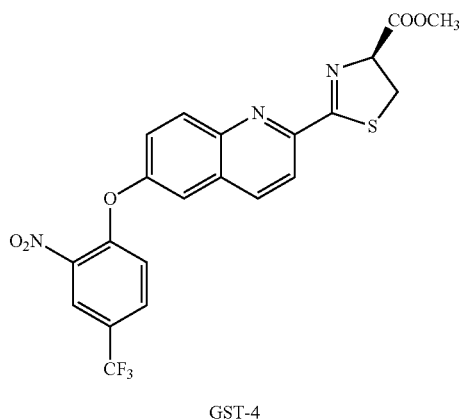

GST-4

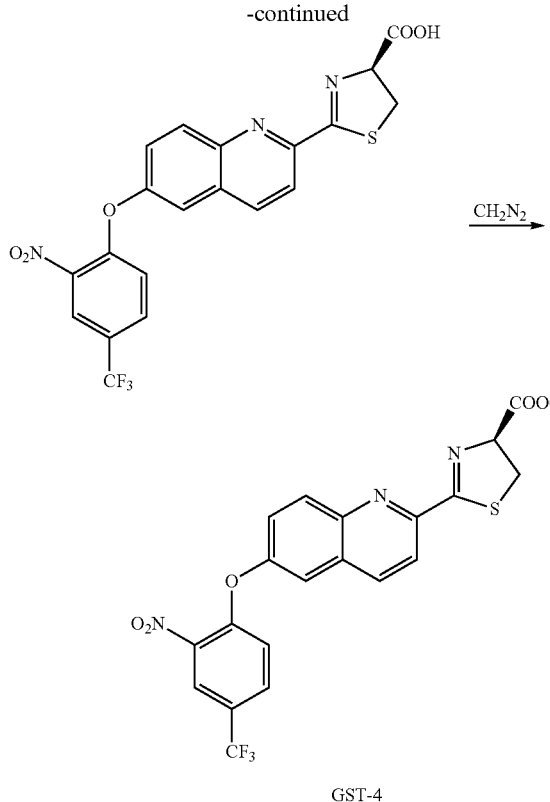

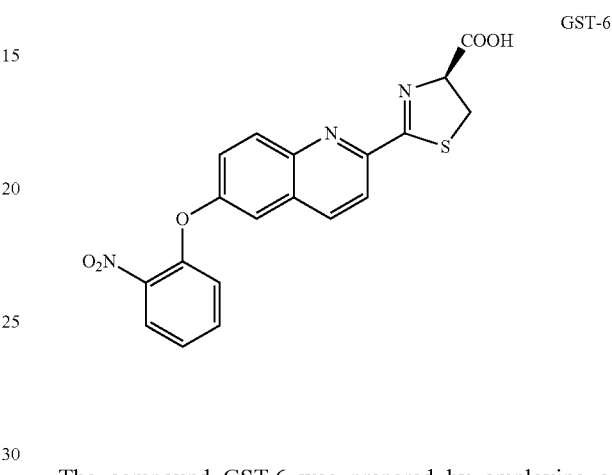

To a mixture of KOH (40%, 6 ml) in 20 ml of ether, N-methyl-n,n-nitrosourea (2.0 g, 0.0194 mol) at 0° C. was added. The resultant mixture was stirred for another 5 minutes. The ether layer was decanted to another flask and dried over KOH at 0° C. To the solution of quioneline luciferin (0.2 g) in 5 mL of THF, the above diazomethane ether solution was until the solution became deep yellow in color. The mixture was stirred for 30 minutes and quenched by adding acetic acid (1 ml). 10 ml of water was added, the mixture extracted three times with ethyl acetate, and dried over $Na_2SO_4$. The compound was purified by flash column using heptanes/ethyl acetate as solvent. $^1$H NMR ($CD_2Cl_2$): 8.23 (s, 1H), 8.0-8.2 (m, 3H), 7.75 (d, 1H), 7.50 (d, 1H), 7.39 (s, 1H), 7.15 (d, 1H), 7.46 (d, 1H), 5.42 (t, 1H, CHCOO), 3.74 (s, 3H, $CH_3$), 3.58 (d, 2H, $CH_2$). MS (ES) m/e (M+1): 478. $\lambda_{max}$ (nm)/$\epsilon_{max}$ (cm$^{-1}$M$^{-1}$): 322/10,800; 328/8,800 in MeOH.

Example 3. Synthesis of 6-(4-nitrophenoxy)quinolinyl-luciferin (GST-5)

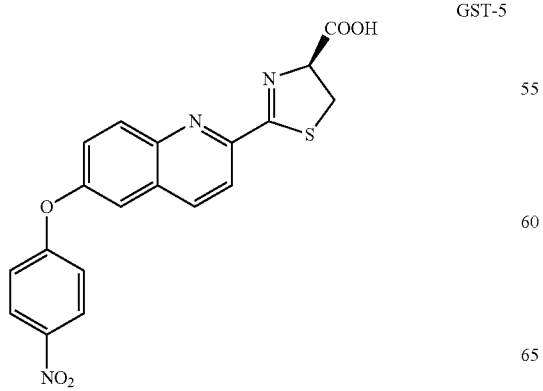

The compound GST-5 was prepared by employing a method similar to the one used for the synthesis of GST-3 (Example 1). $^1$H NMR ($d_6$-DMSO): 8.39 (d, 1H), 8.28 (d, 2H), 8.19 (m, 2H), 7.74 (s, 1H), 7.60 (d, 1H), 7.28 (s, 1H), 5.37 (t, 1H, CHCOO), 3.59 (d, 2H, $CH_2$). MS (ES) m/e (M+2): 397. $\lambda_{max}$ 328 nm, $\epsilon_{max}$ 17,200 cm$^{-1}$M$^{-1}$ in MeOH.

Example 4. Synthesis of 6-(2-nitrophenoxy)quinolinyl-luciferin (GST-6)

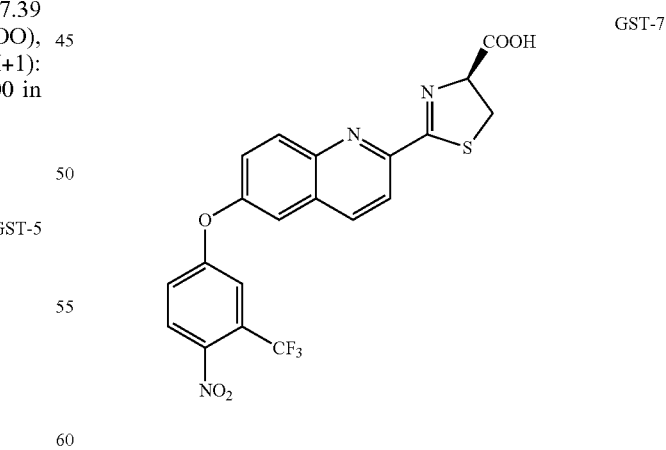

The compound GST-6 was prepared by employing a method similar to the one used for the synthesis of GST-3 (Example 1). $^1$H NMR ($d_6$-DMSO): 8.39 (d, 1H), 8.13 (m, 3H), 7.78 (t, 1H), 7.63 (d, 1H), 7.56 (s, 1H), 7.48 (t, 1H), 7.38 (d, 1H), 5.37 (t, 1H, CHCOO), 3.59 (m, 2H, $CH_2$). MS (ES) m/e (M+2): 397. $\lambda_{max}$ (nm)/$\epsilon_{max}$ (cm$^{-1}$M$^{-1}$): 323/10, 400; 327/9,500; 337/8,300 in MeOH.

Example 5. Synthesis of 6-(3-trifluoromethyl-4-nitrophenoxy)quinolinyl-luciferin (GST-7)

The compound GST-7 was prepared by employing a method similar to the one used for the synthesis of GST-3 (Example 1). $^1$H NMR ($d_6$-DMSO): 8.47 (d, 1H), 8.15-8.30 (m, 3H), 7.85 (d, 1H), 7.78 (d, 1H), 7.73 (dd, 1H), 7.55 (d, 1H), 5.45 (t, 1H, CHCOO), 3.5-3.7 (m, 2H, $CH_2$). MS (ES) m/e (M+1): 464. $\lambda_{max}$ 321 nm, $\epsilon_{max}$ 11,000 cm$^{-1}$M$^{-1}$ in MeOH.

Example 6. Synthesis of 6-(2-trifluoromethyl-4-nitrophenoxy)quinolinyl-luciferin (GST-8)

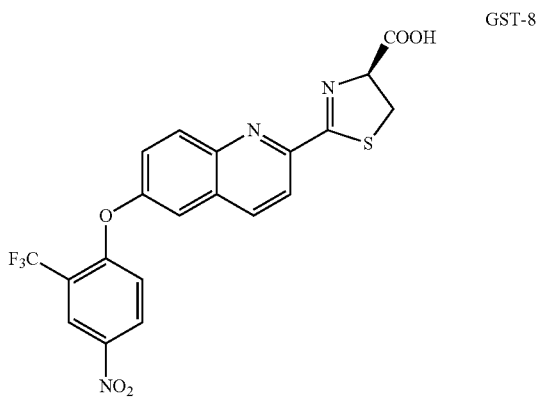 [SMILES: O=C(O)[C@H]1CSC(c2ccc3cc(Oc4ccc([N+](=O)[O-])cc4C(F)(F)F)ccc3n2)=N1]

The compound GST-8 was prepared by employing a method similar to the one used for the synthesis of GST-3 (Example 1). $^1$H NMR (d$_6$-DMSO): 8.56 (d, 1H), 8.47 (d, 2H), 8.20 (dd, 2H), 7.92 (d, 1H), 7.72 (dd, 1H), 7.33 (d, 1H), 5.44 (t, 1H, CHCOO), 3.5-3.7 (m, 2H, CH$_2$). MS (ES) m/e (M+1): 464. $\lambda_{max}$ 328 nm, $\epsilon_{max}$ 10,100 cm$^{-1}$M$^{-1}$ in MeOH.

Example 7. Synthesis of 6-(5-trifluoromethyl-2-nitrophenoxy)quinolinyl-luciferin (GST-9)

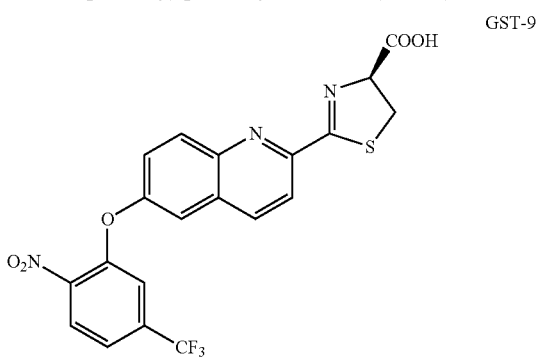 [SMILES: O=C(O)[C@H]1CSC(c2ccc3cc(Oc4cc(C(F)(F)F)ccc4[N+](=O)[O-])ccc3n2)=N1]

The compound GST-9 was prepared by employing a method similar to the one used for the synthesis of GST-3 (Example 1). $\lambda_{max}$ (nm)/$\epsilon_{max}$ (cm$^{-1}$M$^{-1}$): 321/10,400; 328/8,300 in MeOH.

Example 8. Synthesis of 6-(4-fluoro-2-nitrophenoxy)quinolinyl-luciferin (GST-10)

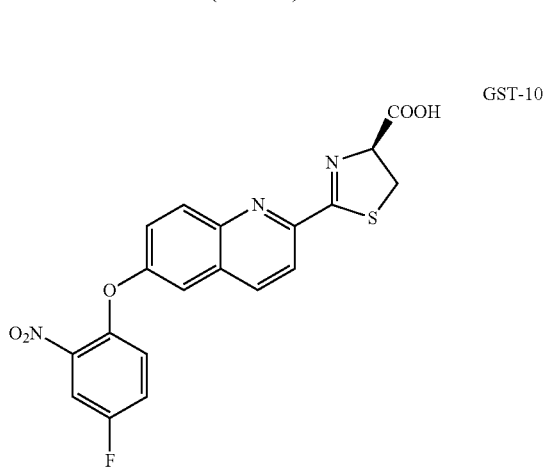

The compound GST-10 was prepared by employing a method similar to the one used for the synthesis of GST-3 (Example 1). $^1$H NMR (d$_6$-DMSO): 8.38 (d, 1H), 8.02-8.2 (m, 3H), 7.6-7.8 (m, 2H), 7.5-7.6 (m, 2H, 1H), 5.34 (t, 1H, CHCOO), 3.5-3.7 (m, 2H, SCH$_2$). MS (ES) m/e (M+2): 415. $\lambda_{max}$ 321 nm, $\epsilon_{max}$ 10,600 cm$^{-1}$M$^{-1}$ in MeOH.

Example 9. Synthesis of 6-(2-nitro-4-methylcarboxylphenoxy)quinolinyl-luciferin (GST-11)

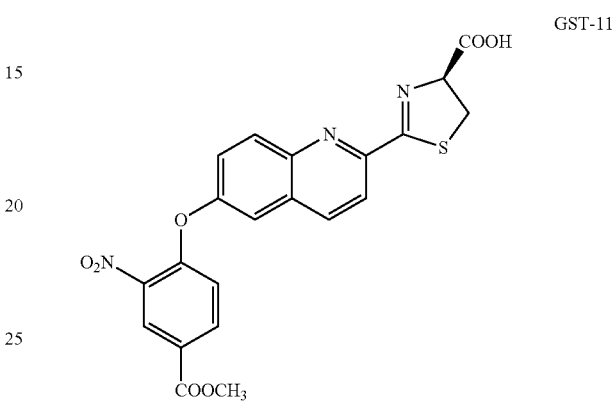

The compound GST-11 was prepared by employing a method similar to the one used for the synthesis of GST-3 (Example 1). $^1$H NMR (d$_6$-DMSO): 8.68 (d, 1H), 8.15-8.30 (m, 2H), 8.1-8.2 (m, 2H), 7.64-7.74 (m, 2H), 7.33 (d, 1H), 5.42 (t, 1H, CHCOO), 3.81 (s, 3H, CH$_3$), 3.5-3.7 (m, 2H, CH$_2$). MS (ES) m/e (M+2): 455. $\lambda_{max}$ 321 nm, $\epsilon_{max}$ 16,200 cm$^{-1}$M$^{-1}$ in MeOH Example 10. Synthesis of 6-(2-Nitro-benzenesulfonic acid) luciferin ester (GST-13)

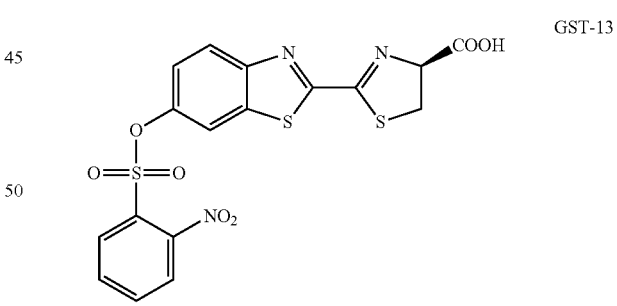

Synthesis of 2-cyano-6-(2-nitro-benzenesulfonic acid)benzothiozole

To a solution of 6-hydroxy-2-cyanobenzothiozole (0.50 g, 2.84 mmol) and 2-nitrobenzene-sulfonyl chloride (0.63 g, 2.84 mmol) in 15 ml of anhydrous methylene chloride, TEA (0.58 g, 5.68 mmol) was added. The resultant mixture was stirred for 3 hours. The product was purified by flash chromatography using heptane/ethyl acetate/methylene chloride (70/30/15) as eluent in a yield of 55%.

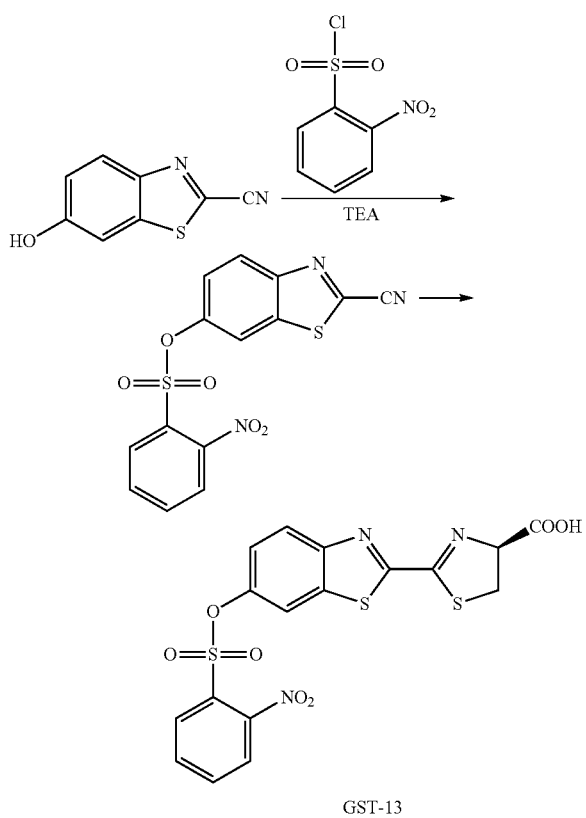

GST-13

Synthesis of GST-13

GST-13 was prepared by employing a method similar to the one used for the synthesis of luciferin GST-3 (Example 1). $^1$H NMR (d$_6$-DMSO): 8.14-8.26 (m, 2H), 8.17 (s, 1H), 8.07 (td, J=7.5 Hz, J=1.3 Hz, 1H), 7.99 (dd, J=8.0 Hz, Hz, J=1.2 Hz, 1H), 7.85 (td, J=7.8 Hz, J=1.2 Hz, 1H), 7.34 (dd, J=9.0 Hz, J=2.4 Hz, 1H), 5.44 (t, J=9.0 Hz, 1H, CH—COOH), 3.6-3.9 (m, 2H, CH$_2$). MS (ES): m/e (M+1), 466. $\lambda_{max}$ 292 nm, $\epsilon_{max}$ 19,100 cm$^{-1}$M$^{-1}$ in MeOH.

Example 11. Synthesis of 6-(4-Nitro-benzenesulfonic acid) luciferin ester (GST-14)

GST-14

The compound GST-14 was prepared by employing a method similar to the one used for the synthesis of GST-13 (Example 10). $^1$H NMR (d$_6$-DMSO): 8.42 (d, 2H), 8.17 (m, 3H), 8.08 (d, 1H), 7.25 (dd, 1H), 5.44 (t, 1H, CH—COOH), 3.6-3.9 (m, 2H, CH$_2$). MS (ES): m/e (M+1), 466. $\lambda_{max}$ 292 nm, $\epsilon_{max}$ 19,400 cm$^{-1}$M$^{-1}$ in MeOH.

Example 12. Synthesis of 6-(2-Nitro-benzenesulfonic acid) quinolinyl-luciferin ester (GST-15)

GST-15

The compound GST-15 was prepared by employing a method similar to the one used for the synthesis of GST-13 (Example 10). $^1$H NMR (d$_6$-DMSO): 8.54 (d, 1H), 7.9-8.3 (m, 6H), 7.85 (t, 1H), 7.57 (dd, 1H), 5.41 (t, 1H, CH—COOH), 3.5-3.7 (m, 2H, CH$_2$). MS (ES): m/e (M+1), 460. $\lambda_{max}$ 285 nm, $\epsilon_{max}$ 9,010 cm$^{-1}$M$^{-1}$ in MeOH.

Example 13. Synthesis of 6-(4-Nitro-benzenesulfonic acid) quinolinyl-luciferin ester (GST-16)

GST-16

The compound GST-16 was prepared by employing a method similar to the one used for the synthesis of GST-13 (Example 10). $^1$H NMR (d6-DMSO): 8.23 (d, J=8.7 Hz, 1H), 8.43 (d, J=8.7 Hz, 2H), 8.18 (m, 3H), 8.13 (d, J=9.3 Hz, 1H), 7.89 (d, J=2.7 Hz, 1H), 7.51 (dd, J=9.3 Hz, J=3 Hz, 1H), 5.42 (dd, J=8.4 Hz, J=8.4 Hz, 1H, CHCOO), 3.5-3.7 (m, 2H, CH$_2$). MS (ES) m/e (M+1): 461. $\lambda_{max}$ 285 nm, $\epsilon_{max}$ 12,400 cm$^{-1}$M$^{-1}$ in MeOH.

Example 14. Synthesis of 6-(2-Nitro-4-trifluorobenzenesulfonic acid) luciferin ester (GST-17)

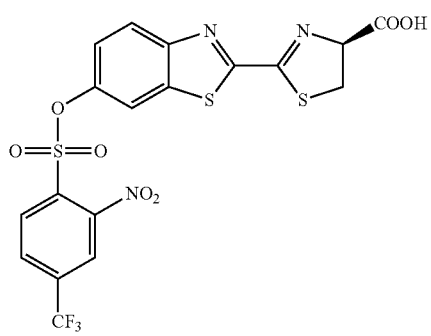

The compound GST-17 was prepared by employing a method similar to the one used for the synthesis of GST-13 (Example 10). $^1$H NMR (d6-DMSO): 8.82 (s, 1H), 8.15-8.30 (m, 4H), 7.43 (d, 1H), 5.43 (t, 1H, CHCOO), 3.6-3.9 (m, 2H, SCH$_2$). MS (ES) m/e (M+1): 534. $\lambda_{max}$ 292 nm, $\epsilon_{max}$ 18,600 cm$^{-1}$M$^{-1}$ in MeOH.

Example 15. Synthesis of 7-(5-trifluoromethyl-2-nitrophenoxy)-4-methyl-coumarin

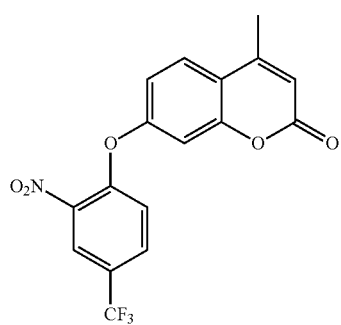 [SMILES: Cc1cc(=O)oc2cc(Oc3ccc(C(F)(F)F)cc3[N+](=O)[O-])ccc12]

The compound was prepared by employing a method similar to the one used for synthesis of the precursor of GST-3 (Example 1). $^1$H NMR (CD$_2$Cl$_2$): 8.37 (s, 1H), 7.88 (d, 2H), 7.70 (m, 2H), 7.28 (d, 1H), 7.05 (d, 1H), 7.00 (s, 1H), 6.25 (s, 1H), 2.43 (s, 3H, CH$_3$). MS (ES) m/e (M+2): 367. $\lambda_{max}$ 320 nm, $\epsilon_{max}$ 12,700 cm$^{-1}$M$^{-1}$ in MeOH

Example 16. Synthesis of bis(-(5-trifluoromethyl-2-nitrophenoxy)-fluorescein lactone

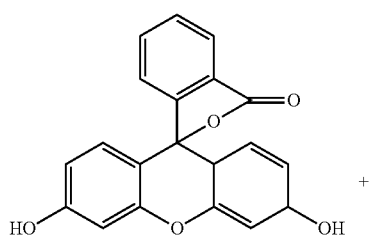

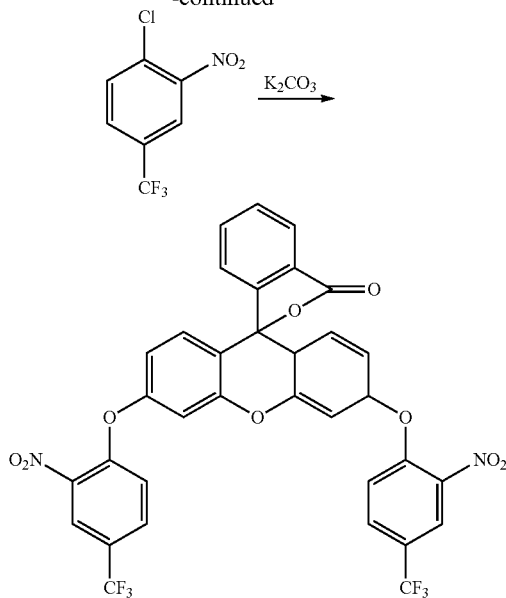

A mixture of fluorescein (2.0 g, 60 mmol), 2-nitro-4-trifluoromethylbenzene chloride (3.0 g, 13.3 mmol) and potassium carbonate (2.0 g, 14.5 mmol) in 50 ml of DMSO was heated to 100° C. for 1 hour. Upon cooling to room temperature, the mixture was poured into 30 ml of cold water and extracted three times with methylene chloride. The combined organic layer was washed with water and dried over magnesium sulfate. The product was purified by flash chromatography using heptane/methylene chloride/ethyl acetate (7/3/0 to 7/3/) as eluent in a yield of 88%. $^1$H NMR (CD$_2$Cl$_2$): 8.28 (s, br, 2H), 8.05 (d, 1H), 7.84 (d, 2H), 7.66-7.82 (m, 2H), 7.26 (d, 2H), 7.03 (d, 2H), 6.92 (d, 2H), 6.84 (dd, 2H).

Example 17. Synthesis of PBI 4146

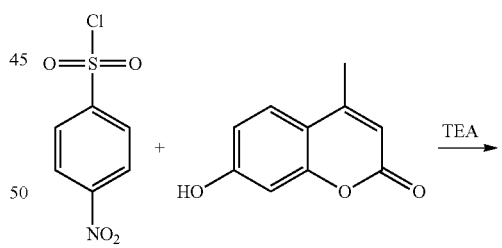

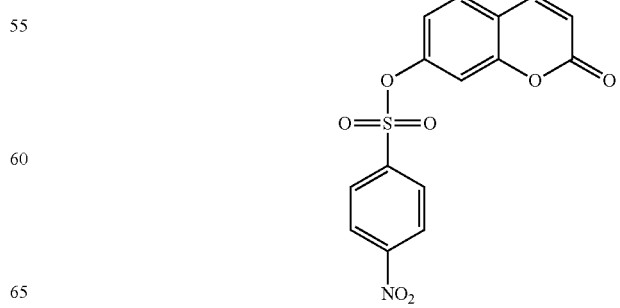

To a solution of p-Nitrobenzene sulfonyl chloride (0.63 g, 2.85 mmol) and 7-hydroxyl-4-methylcoumarin (0.5 g, 2.84 mmol) in 20 ml of CH$_2$Cl$_2$, TEA (0.29 g, 0.4 ml) was added. The resultant mixture was stirred for 30 minutes. The compound was purified by flash chromatography using heptane/CH$_2$Cl$_2$ and ethyl acetate as eluent in a yield of 87%. $^1$H NMR (CD$_2$Cl$_2$): 8.4 (d, 2H), 8.08 (d, 2H), 7.6 (d, 1H), 6.9-7.19 (m, 2H), 6.27 (s, 1H), 2.4 (s, 3H). MS (m+/z): 362.0 (M+1).

Example 18. Synthesis of PBI 4153

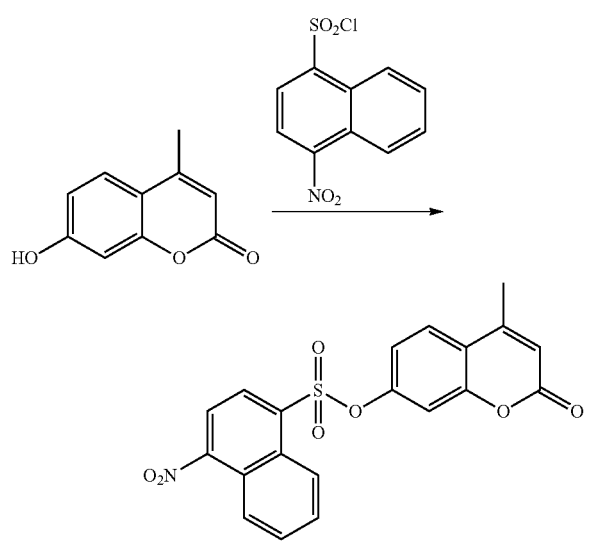

7-Hydroxy-4-methylcoumarin (0.17 g, 0.97 mmol) was dissolved in dichloromethane (10 ml) with triethylamine (0.18 g, 1.78 mmol). 4-nitronaphthalene-1-sulfonyl chloride (0.33 g, 1.21 mmol) was added portionwise. The reaction mixture was stirred for 4 hours and was extracted with ethyl acetate and water. The organic phase was collected and dried over sodium sulfate. After filtration, the solvent was evaporated, and the residue was purified by flash chromatography (heptanes/ethyl acetate: 1/1) to give the product (0.35 g, 87%). $^1$H NMR (300 MHz, CD$_2$Cl$_2$, δ): 8.95 (m, 1H), 8.42 (m, 1H), 8.24 (d, J=9 Hz, 1H), 7.97 (m, 3H), 7.51 (d, J=6 Hz, 1H), 6.92 (m, 2H), 6.23 (d, 1H), 2.36 (m, 3H); MS (ESI) m/z 412.1 (M+1).

Example 19. Synthesis of GST-21

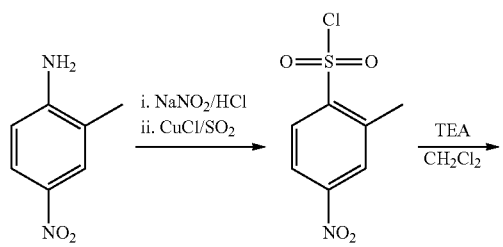

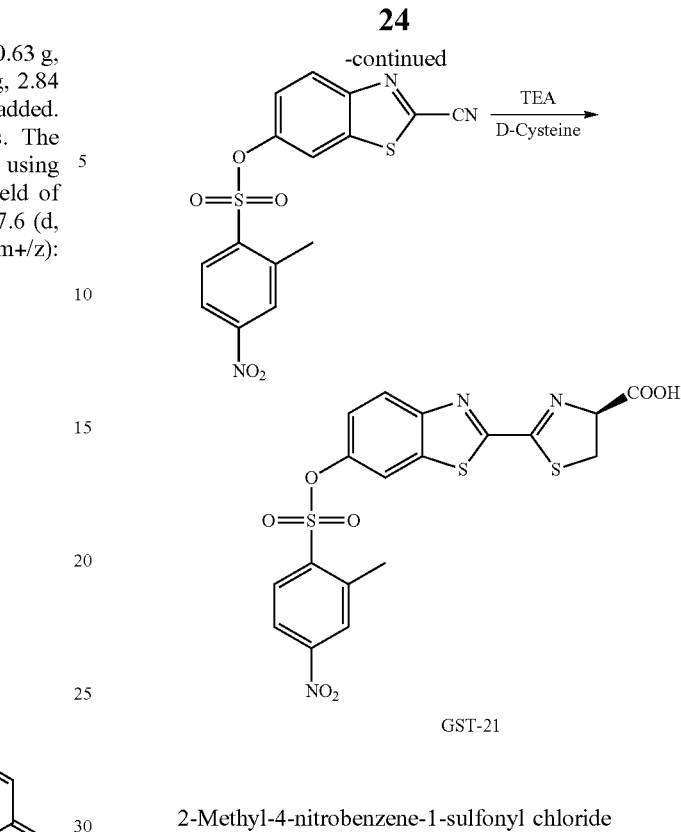

GST-21

2-Methyl-4-nitrobenzene-1-sulfonyl chloride

To the mixture of concentrated HCl (30 ml) and acetic acid (10 ml), aromatic amine (10.0 g, 65.7 mmol) in one portion with stirring at room temperature was added. A white hydrochloride salt was formed immediately, and the resultant mixture was cooled to −15° C. A solution of sodium nitrite (5.44 g, 78.9 mmol) in 15 ml of water was added dropwise while the temperature was kept at −5° C. to −10° C., and the resultant mixture was then stirred for 45 minutes at this temperature range. Sulfur dioxide was bubbled through acidic acid (70 ml) for 30 minutes at 0° C. To the solution, copper (I) chloride (1.65 g) was added, and the mixture continued to bubbling in sulfur dioxide at 0° C. until the solution appeared slightly blue in color (about another 30 minutes). The above diazonium solution was added to the sulfur dioxide solution at 0° C. and stirred for 10 minutes at 0° C. The mixture was then poured into ice-water and extracted three times with ether. The combined organic layer was washed with brine and dried with magnesium sulfate. After removal of the solvent, the product was purified by flash chromatography using heptane/methylene chloride (7/3 to 6/4) as eluent (yield 29%). $^1$H NMR (CD$_2$Cl$_2$) δ(ppm): 8.12 (d, J=8.1 Hz, 1H), 7.67 (s, 1H), 7.64 (d, J=8.4 Hz, 1H).

2-Cyanobenzothiazol-6-yl 2-methyl-4-nitrobenzenesulfonate

To the solution of benzene sulfonyl chloride derivative (0.7 g, 2.98 mmol) and 2-cyano-6-hydroxoylbenzothiazole or 2-cyano-6-hydroxyquinoline (2.84 mmol) in 10 ml of dry methylene chloride, triethylamine (0.58 g, 5.68 mmol) at room temperature was added, and the resultant mixture stirred for 3 hours. The product was purified by flash chromatography using heptane/methylene chloride (1/2) as eluent. (yield 85%): $^1$H NMR (CDCl$_3$) δ(ppm): 8.30 (d, J=2.0 Hz, 1H), 8.16 (d, J=9.3 Hz, 1H), 8.13 (dd, J=8.7 Hz, J=2.0 Hz, 1H), 8.04 (d, J=8.7 Hz, 1H), 7.78 (d, J=2.4 Hz, 1H), 7.27 (dd, J=9.0 Hz, J=2.4 Hz, 1H), 2.95 (s, 3H, CH₃). MS (ES) m/e (M+1): 376.

Luciferin 2-methyl-4-nitrobenzenesulfonate (GST-21)

To the solution of nitrobenzene sulfonate derivative (1.07 mmol) and D-cysteine (1.28 mmol) in methanol (20 ml), CH₂Cl₂ (10 ml) and H₂O (5 ml), triethylamine (1.6 mmol) was added. The mixture was stirred at room temperature for 30-60 minutes and then neutralized to slightly acidic with acidic acid. After removal of organic solvent under vacuum, the solid was collected by filtration, washed three times with water and purified by flash chromatography using methylene chloride/methanol (90/10) as eluent. The product was solidified in cold ether, and the white powder collected by filtration and dried under vacuum. (yield 62%): ¹H NMR (d₆-DMSO) δ(ppm): 8.48 (s, 1H), 8.1-8.2 (m, 2H), 8.08 (d, J=2.4 Hz, 1H), 8.01 (d, J=8.7 Hz, 1H), 7.27 (dd, J=8.7 Hz, J=2.4 Hz, 1H), 5.453 (t, J=8.7, 1H, CH—COOH), 3.6-3.9 (m, 2H, CH₂), 2.84 (s, CH₃, 3H). MS (ES): m/e (M+1), 480. λ$_{max}$ 293 nm, ε$_{max}$ 19,700 cm⁻¹M⁻¹ in MeOH.

Example 20. Synthesis of GST-22

GST-22 was prepared by employing a method similar to the one used for the synthesis of GST-21 (Example 19).

2-Nitro-4-methylbenzenesulfonyl chloride (yield 53%)

¹H NMR (CDCl₃) δ(ppm): 8.13 (d, J=8.4 Hz, 1H), 7.67 (s, 1H), 7.61 (d, J=8.1 Hz, 1H).

2-Cyanobenzothiazol-6-yl 2-nitro-4-methylbenzenesulfonate (yield 67%)

¹H NMR (CD₂Cl₂) δ(ppm): 8.23 (d, J=9.0 Hz, 1H), 8.02 (d, J=2.4 Hz, 1H), 7.82 (d, J=8.4 Hz, 1H), 7.80 (s, 1H), 7.5-7.6 (m, 2H), 2.58 (s, 3H, CH₃). MS (ES) m/e (M+1): 376.

Luciferin 2-nitro-4-methylbenzenesulfonate (GST-22) (yield 62%)

¹H NMR (d₆-DMSO) δ(ppm): 8.18 (d, J=9.0 Hz, 1H), 8.16 (d, J=2.4 Hz, 1H), 8.06 (s, 1H), 7.84 (d, J=8.1 Hz, 1H), 7.65 (d, J=8.1 Hz, 1H), 7.33 (dd, J=9.0 Hz, J=2.4 Hz, 1H), 5.44 (dd, J=8.7, J=8.7 Hz, 1H, CH—COOH), 3.6-3.9 (m, 2H, CH₂), 2.48 (s, CH₃, 3H, overlap with DMSO). MS (ES): m/e (M+1), 480. λ$_{max}$ 292 nm, ε$_{max}$ 20,500 cm⁻¹M⁻¹ in MeOH.

Example 21. Synthesis of GST-23

GST-23 was prepared by employing a method similar to the one used for the synthesis of GST-21 (Example 19).

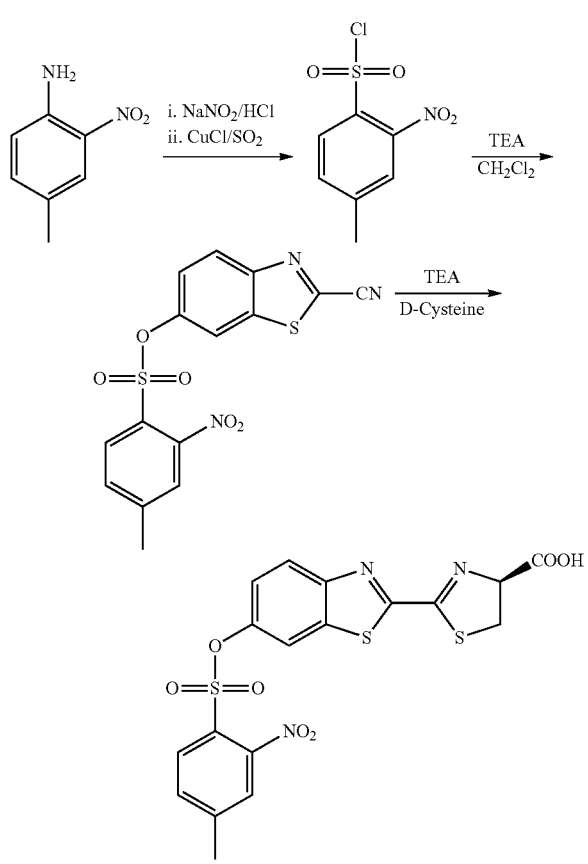

GST-22

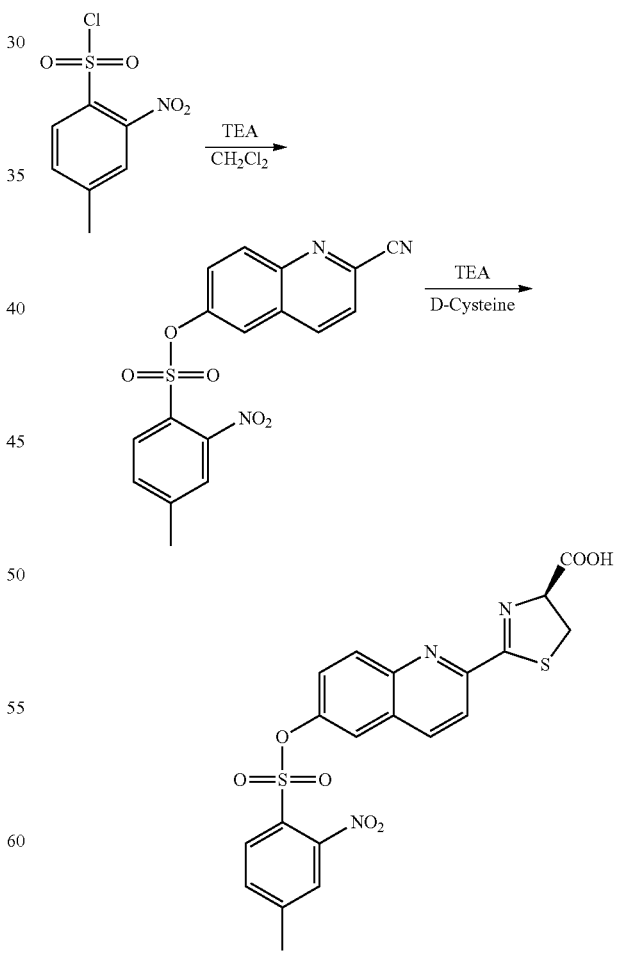

GST-23

2-Cyanoquinolin-6-yl
2-nitro-4-methylbenzenesulfonate (yield 40%)

$^1$H NMR (CD$_2$Cl$_2$) δ(ppm): 8.34 (d, J=8.4 Hz, 1H), 8.16 (d, J=9.3 Hz, 1H), 7.82 (d, J=2.7 Hz, 1H), 7.81 (d, J=8.1 Hz, 1H), 7.69 (s, 1H), 7.66 (dd, J=9.0 Hz, J=2.7 Hz, 1H), 7.47 (d, J=8.1 Hz, 1H), 2.52 (s, CH$_3$, 3H). MS (ES) m/e (M+1): 370.

Quinolinyl-luciferin
2-nitro-4-methylbenzenesulfonate (GST-23) (yield 55%)

$^1$H NMR (d$_6$-DMSO) δ(ppm): 8.55 (d, J=8.4 Hz, 1H), 8.19 (d, J=8.4 Hz, 1H), 8.13 (d, J=9.0 Hz, 1H), 8.07 (s, 1H), 7.98 (d, J=3.0 Hz, 1H), 7.87 (d, J=8.4 Hz, 1H), 7.65 (d, J=8.1 Hz, 1H), 7.33 (dd, J=9.3 Hz, J=3.4 Hz, 1H), 5.45 (dd, J=8.7, J=8.7 Hz, 1H, CH—COOH), 3.5-3.8 (m, 2H, CH$_2$), 2.48 (s, CH$_3$, 3H, overlap with DMSO). MS (ES): m/e (M+1), 474. λ$_{max}$ 286 nm, ε$_{max}$ 11,500 cm$^{-1}$M$^{-1}$ in MeOH.

Example 22. Synthesis of GST-24

GST-24 was prepared by employing a method similar to the one used for the synthesis of GST-21 (Example 19).

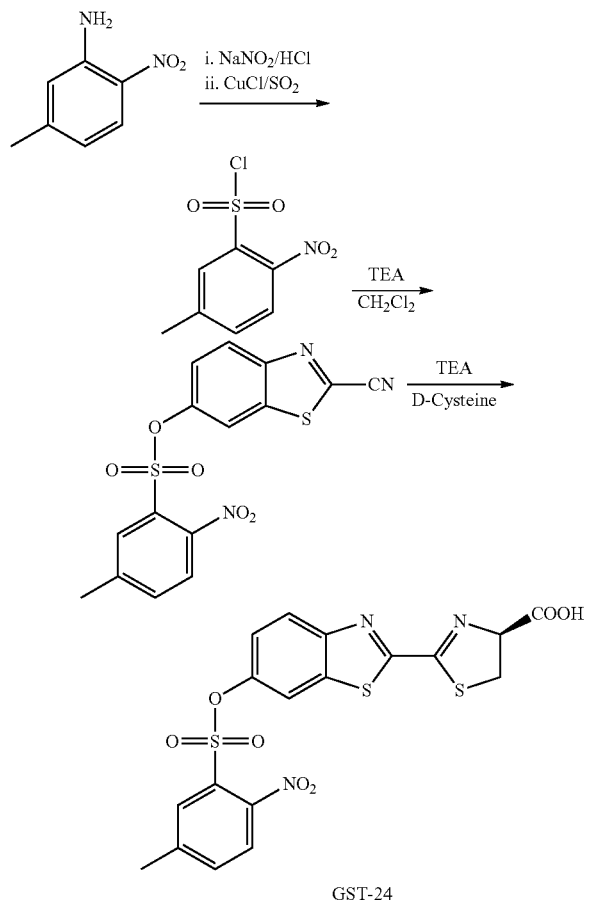

GST-24

2-Nitro-5-methylbenzenesulfonyl chloride (yield 33%)

$^1$H NMR (CD$_2$Cl$_2$) δ(ppm): $^1$H NMR (CDCl$_3$) δ(ppm): 8.05 (d, J=8.4 Hz, 1H), 7.81 (s, 1H), 7.68 (d, J=8.1 Hz, 1H).

2-Cyanobenzothiazol-6-yl
2-nitro-5-methylbenzenesulfonate (yield 85%)

$^1$H NMR (CD$_2$Cl$_2$) δ(ppm): 8.21 (d, J=9.0 Hz, 1H), 7.96 (d, J=2.4 Hz, 1H), 7.83 (d, J=8.4 Hz, 1H), 7.80 (s, 1H), 7.66 (d, J=8.4 Hz, 1H), 7.52 (dd, J=9.0 Hz, J=2.4 Hz, 1H), 2.46 (s, CH$_3$, 3H). MS (ES) m/e (M+1): 376.

Luciferin 2-nitro-5-methylbenzenesulfonate (GST-24) (yield 48%)

$^1$H NMR (d$_6$-DMSO) δ(ppm): 8.18-8.22 (m, 2H), 8.11 (d, J=8.4 Hz, 1H), 7.80-7.98 (m, 2H), 7.36 (dd, J=9.0 Hz, J=2.4 Hz, 1H), 5.44 (dd, J=8.7, J=8.7 Hz, 1H, CH—COOH), 3.6-3.9 (m, 2H, CH$_2$), 2.42 (s, CH$_3$, 3H). MS (ES): m/e (M+1), 480. λ$_{max}$ 292 nm, ε$_{max}$ 19,700 cm$^{-1}$M$^{-1}$ in MeOH.

Example 23. Synthesis of GST-25

GST-25 was prepared by employing a method similar to the one used for the synthesis of GST-21 (Example 19).

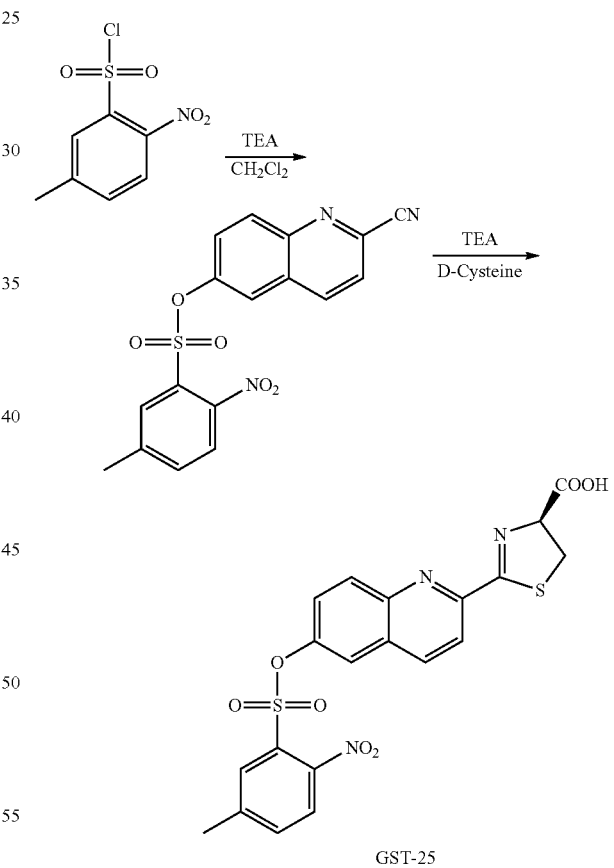

GST-25

2-Cyanoquinolin-6-yl
2-nitro-5-methylbenzenesulfonate (yield 56%)

$^1$H NMR (CD$_2$Cl$_2$) δ(ppm): 8.34 (d, J=8.1 Hz, 1H), 8.18 (d, J=9.3 Hz, 1H), 7.80-7.86 (m, 3H), 7.78 (d, J=8.7 Hz, 1H), 7.69 (dd, J=9.6 Hz, J=2.7 Hz, 1H), 7.65 (d, J=8.4 Hz, 1H), 2.58 (s, CH$_3$, 3H). MS (ES) m/e (M+1): 370.

Quinolinyl-luciferin 2-nitro-5-methylbenzenesulfonate (GST-25) (yield 42%)

$^1$H NMR (d$_6$-DMSO) δ(ppm): 8.56 (d, J=9.0 Hz, 1H), 8.20 (d, J=8.7 Hz, 1H), 8.15 (d, J=9.3 Hz, 1H), 8.11 (d, J=8.4 Hz, 1H), 8.0 (d, J=2.7 Hz, 1H), 7.89 (s, 1H), 7.85 (d, J=8.1 Hz, 1H), 7.59 (dd, J=9.3 Hz, J=2.7 Hz, 1H), 5.45 (dd, J=8.7, J=8.7 Hz, 1H, CH—COOH), 3.5-3.8 (m, 2H, CH$_2$), 2.49 (s, CH$_3$, 3H). MS (ES): m/e (M+1), 474. $\lambda_{max}$ 285 nm, $\epsilon_{max}$ 11,600 cm$^{-1}$M$^{-1}$ in MeOH.

Example 24. Measurement of Glutathione-S-Transferase (GST) or Reduced Glutathione (GSH) Using a Luciferin Derivative A luciferin derivative, GST-3, was prepared as a substrate for GST and tested in a two step format. In the first step, GST-3 was added to a mixture containing a GST enzyme with or without glutathione. At different times after reaction initiation, a portion of the reaction was mixed with a luciferase reaction mixture. Reactions in which light production increased over time indicate that the derivative, GST-3, is a substrate for GST and can be used in an assay to detect GST and/or reduced glutathione (GSH).

Various GST enzyme forms were used to test the use of GST-3 as a substrate for GST to detect GST or GSH. Reactions were assembled in individual 0.5 ml microfuge tubes as indicated in Table 1. All components except for the GST enzyme were added. The GST enzyme form was then added to the reactions as indicated in Table 1, and the reactions mixed. At 0.1, 5, 10 and 15 minutes, 10 µl of each reaction was mixed with 90 µl Luciferin Detection Solution (Luciferin Detection Reagent (Promega) mixed with P450-G10 Buffer (Promega)), and luminescence detected immediately using a Turner TD 20/20 Luminometer (Promega). Luminescence values (RLUs) are indicated in Table 2.

TABLE 1

|  | 1 | 2 | 3 | 4 | 5 | 6 | 7 | 8 |
| --- | --- | --- | --- | --- | --- | --- | --- | --- |
| 12 mM GST-3 in acetonitrile | 5 µl | 5 µl | 5 µl | 5 µl | 5 µl | 5 µl | 5 µl | 5 µl |
| 1M BisTris pH 6.6 | 5 µl | 5 µl | 5 µl | 5 µl | 5 µl | 5 µl | 5 µl | 5 µl |
| 100 mM Glutathione |  | 2 µl |  | 2 µl |  | 2 µl |  | 2 µl |
| 6 mg/ml S. japonica GST (Sigma) |  |  | 5 µl | 5 µl |  |  |  |  |
| 5 mg/ml porcine GST (Sigma) |  |  |  |  | 5 µl | 5 µl |  |  |
| 5 ml/ml equine GST (Sigma) |  |  |  |  |  |  | 5 µl | 5 µl |
| Water | 90 µl | 88 µl | 85 µl | 83 µl | 85 µl | 83 µl | 85 µl | 83 µl |

TABLE 2

| Time (minutes) | 1 | 2 | 3 | 4 | 5 | 6 | 7 | 8 |
| --- | --- | --- | --- | --- | --- | --- | --- | --- |
| 0.1 | 33.26 | 35.72 | 32.67 | 32.57 | 46.95 | 71.1 | 30.42 | 252.2 |
| 5 | 38.2 | 36.07 | 32.42 | 40.79 | 51.85 | 269.1 | 32.98 | 3662 |
| 10 | 32.17 | 40.85 | 38.65 | 48.64 | 51.15 | 463.2 | 38.75 | 7629 |
| 15 | 35.53 | 46.43 | 33.82 | 61.54 | 48.41 | 619.3 | 38.39 | 9324 |

Luminescence obtained from reactions without glutathione (#1, 3, 5 and 7) did not increase greatly over time. However, luminescence in reactions containing both glutathione and GST (#2, 4, 6 and 8) increased substantially over time. This demonstrates that the action of GST in combination with glutathione results in the conversion of the luciferin derivative, GST-3, into a substrate for luciferase which can be used in a luciferase-based reaction. Therefore, GST-3 is a substrate for GST, and it can be used to detect GST and/or GSH.

Example 25. Fluorescent Detection of GSSG Using a Luciferin Derivative

The following example demonstrates that fluorescent detection of GSSG can be achieved using a luciferin derivative substrate for GST.

To a 96-well, black-walled, clear bottom plate, 10 µl of 1× Passive Lysis Buffer (PLB; Promega) was added to half the wells, and 10 µA of N-ethyl maleimide (NEM; Sigma; 50 ul of 50 mM NEM in DMSO diluted to 2.5 ml in 1×PLB) was added to the other half of the wells.

Various conditions were then tested in the presence or absence (1×PLB only) of NEM:
1. Titration (0, 5, 10, 15, 20 and 25 uM) reduced glutathione (GSH; Sigma; 1 ul of 100 mM diluted in 1 ml 1×PLB);
2. Titration (0, 5, 10, 15, 20 and 25 uM) oxidized glutathione (GSSG; Sigma; 2 ul of 10 mM diluted in 1 ml 1×PLB);
3. Titration (0, 5, 10, 15, 20 and 25 uM) oxidized glutathione in the presence of a high concentration (25 uM) reduced glutathione/GSH.
4. No gluthathione control After addition of the appropriate mixtures to the appropriate wells, 20 µl of a mixture of DTT and GST-22 (150 µl of 100 mM and 240 µl GST-22 (Promega) diluted in 100 mM HEPES pH 7.5) was added to each sample. Fluorescence was imaged on an Ambis System (Alpha Innotech Corporation) using a transilluminator UV excitation (Alpha Innotech Corporation) and analyzing using Fluor Chem 8000 software (Alpha Innotech Corporation).

After imaging, 20 µl GST (450 µl GST (Promega) diluted in 3 mls of 100 mM HEPES pH 7.5) was added to all samples. The plate was again imaged as above at several different time points (3, 10, 20 and 30 minutes).

To confirm the fluorescent readings, luminescent readings were taken after fluorescent imaging. 40 µl of each reaction was transferred to a 96-well luminometer plate, and 40 µl GSH-Glo Luciferin Assay Reagent (Promega) added to all wells. Luminescence was then detected on a GloMax® Luminometer (Promega). Luminescence values in relative light units (RLUs) are given in Table 3 (FIG. 4). The duplicate wells were averaged and are listed in Table 4 and 5 (FIG. 4). In Tables 4 and 5, the results from the no GSSG samples were placed in the zero concentration position in the tables to simplify interpretation of the results.

Expected Results

Titration of Reduced Glutathione:

Increasing amounts of reduced glutathione—if not exposed to NEM—is expected to generate increasing concentrations of luciferin over time through the action of GST.

However, if the reduced glutathione is treated with NEM prior to addition of enzyme, the signal should essentially be lost as NEM would react with the reduced glutathione to produce a new chemical species that is not used by GST to convert the pre-luciferin to luciferin. If this is correct, increasing fluorescence should be seen with increasing time and glutathione concentration in samples containing NEM and, in addition, an increase in luminescence is expected with increasing glutathione concentrations. On the other hand, very little fluorescence or luminescence above the "no compound" samples is expected to be seen in the wells containing NEM).

Titration of Oxidized Glutathione:

Increasing amounts of oxidized glutathione is also expected to generate with increasing concentrations of luciferin over time through the action of GST as the reducing agent (DTT) was also added to each sample, thus reducing the GSSG and inactivating NEM in the samples. Since GSSG is not alkylated by NEM, unless it is first reduced to GSH, similar light increases are expected in the samples containing the GSSG titrations over time and GSSG concentration.

Titration of Oxidized Glutathione in the Presence of a High Level of Reduced Glutathione:

Since these samples were given a high level of reduced glutathione, the samples that do not also contain NEM are expected to give a very high signal and may not, in fact, show much additional increase in fluorescence or luminescence in the GSSG titration since additional signal from the GSSG would be added to that from the reduced glutathione. Samples containing NEM, high amounts of GSH, and a varying amount of GSSG are expected to have the signal from the reduced glutathione eliminated by the NEM, and thus the rate of increase of fluorescence and luminescence are expected to be similar to those samples given GSSG without added reduced glutathione.

Actual Results

Reduced Glutathione Wells with No Added NEM:

Samples of the imaged plate containing the titration of reduced glutathione without added NEM show a time and glutathione dependent rate of increase in fluorescence, as expected. This confirms that the luciferin produced in these wells can be detected by measuring fluorescence, and the level of fluorescence is proportional to the amount of reduced glutathione present in the solution. Also, as expected, an increase in luminescence was seen as the amount of added glutathione increased (FIG. 4).

Reduced Glutathione Wells with Added NEM:

Samples of the imaged plate containing the titration of reduced glutathione with NEM present show very little increase in fluorescence, as expected, as NEM was expected to neutralize the signal generated by the addition of GSH. Also, as expected, very little difference in luminescence was seen in the samples not containing GSH, and those containing the highest levels of GSH (compare Tables 4 and 5 (FIG. 4)).

Oxidized Glutathione Wells without Added GSH with or without NEM Addition:

Samples of the imaged plate containing the titration of oxidized glutathione in the presence or absence of NEM show a time and glutathione dependent rate of fluorescence increase, as expected. This confirms that the luciferin produced in these wells can be detected fluorescently, and the level of fluorescence is proportional to the amount of oxidized glutathione present. Also, as expected, an increase in luminescence was seen from these samples as the amount of glutathione added increased. In addition, the values measured in the absence of NEM are similar to those measured in the presence of NEM (compare Tables 4 and 5 (FIG. 4)).

Oxidized Glutathione Wells Titrated in the Presence of High Reduced Glutathione but in the Absence of NEM:

Samples of the imaged plate containing the titration of oxidized glutathione in the presence of high concentrations of reduced glutathione, but without NEM, show a time dependent increase in fluorescence with the level of fluorescence much greater than that seen for the titration of oxidized glutathione in the absence of reduced glutathione. This was expected since the total level of glutathione present for signal generation in these wells is very high. Also, as expected, there was very strong luminescence in these samples (Table 4 (FIG. 4)).

Oxidized Glutathione Wells Titrated in the Presence of High Level Reduced Glutathione and NEM:

Samples of the imaged plate containing the titration of oxidized glutathione in the presence of a high level of reduced glutathione and NEM show a time dependent increase in fluorescence with the level of fluorescence very similar to the wells containing the titration of oxidized glutathione without added GSH. This was expected since the signal generating potential of the reduced glutathione should have been eliminated by the NEM, and thus any signal generated should have been the result of the oxidized glutathione added to the well. Also, as expected, luminescence from these samples are very similar to those from the wells given oxidized glutathione alone (compare Tables 4 and 5 (FIG. 4)) and much lower than those measured from samples containing GSSG in the presence of 25 µM GSH and in the absence of NEM (Table 4 (FIG. 4)).

Although not a highly fluorescent compound, the results demonstrate that fluorescent detection of GSSG can be done using a luciferin derivative. In addition, the signal from GSSG in a sample can be measured in samples containing high concentrations of GSH if proper sample treatment is performed. Yet, by using the methods of this invention, such measurements can be made rapidly and easily and without requiring any protein removal steps.

Example 26. GSSG Measurement with Other Luciferin Derivatives

Solid GST luciferin derivatives, GST 30 and GST 28, were dissolved in DMSO to create 4 mg/ml solutions.

Oxidized glutathione was serially diluted from a 10 mM stock in water to 0, 0.1, 0.5 and 2.5 uM into three different 96-well luminometer plates with duplicate reactions performed. A 30 µl sample of the GST 30 stock was diluted to 3 ml with GSH Glo Reaction Buffer (Promega), and 25 µl added to one of the plates ("30"). A 30 µl sample of GST 28 was diluted to 3 ml with GSH Glo Reaction Buffer, and 25 µl added to a second plate ("28"). A 110 µL sample of GST-22 was diluted to 3 ml with GSH Glo Reaction Buffer, and 25 µl added to the third plate ("GST-22" or "NT"). 50 µl of GSH Glo Reaction Buffer was then added to half the samples of each plate. 25 µl GSH Glo Reaction Buffer with DTT (150 µl of 100 mM DTT to 15 ml of GSH Glo Reaction Buffer) was added to the other half of the samples in each of the plates.

A 60 µl sample of GST (Promega) was diluted to 1 ml with GSH Glo Reaction Buffer, and 50 µl added to duplicate columns of each plate. After a 30 minute incubation at room temperature, 100 µl of GSH Glo Luciferin Assay Reagent (Promega) was added to each sample, and luminescence read 15 minutes later using a luminometer. The resulting luminescence was collected, and the duplicates averaged. The luminescence measured in the absence of GSSG was subtracted from that of the three GSSG concentrations, and the resulting values are presented in Table 6.

TABLE 6

|  | GSSG [µM] | No DTT | With DTT | GST with DTT |
|---|---|---|---|---|
| GST 30 | 2.5 | −147 | −778 | 562244 |
|  | 0.5 | 165 | −472 | 118855 |
|  | 0.1 | −463 | −803 | 11942 |
|  | 0.0 | 0 | 0 | 0 |
| GST 28 | 2.5 | −245 | 1002 | 3699902 |
|  | 0.5 | −13 | 1521 | 422370 |
|  | 0.1 | 454 | 1929 | 131892 |
|  | 0.0 | 0 | 0 | 0 |
| GST-22 | 2.5 | −1456 | −220 | 1980421 |
|  | 0.0 | 0 | 0 | 0 |

Reactions with either GST 30 or GST 28 showed strong luminescence proportional to the amount of GSSG present in the reaction while only very modest luminescence changes were seen in reactions without enzyme and DTT or without enzyme but with DTT. Thus, GST 30 and GST 28 could also be used for GSSG measurement in the method of the present invention.

Example 27. Fluorescent Detection of Glutathione Using Coumarin Derivatives

In this example, a fluorescent light signal is generated from Coumarin derivatives through the use of GST and glutathione.

A Prionex® solution was made by mixing 200 µl of 10% Prionex® (Sigma) with 9.8 ml of 10 mM potassium phosphate buffer, pH 7.4, and 75 µl added to all wells of a 96-well, microtiter plate ("sample plate"). Stock solutions (2 mg/ml) of the GST enzymes GST (Promega Corp. V689B), GST A, GST B, and GST P (purified to have less than 1 mole of GSH per mole of protein) were diluted by addition of 12 ul of the enzyme to 150 ul of 10 mM Potassium Phosphate buffer pH 7.4/Prionex solution. These diluted stocks were then added to the wells. 75 ul of the diluted stocks were added to the wells in row A, and 75 ul transferred from row A through to row H to generate 1:1 serially diluted enzyme solutions.

To a different, 96-well microtiter plate, 25 µl of diluted PBI 4153 (25 µl 1 mg/ml solution of PBI 4153 with 5 ml of 10 mM potassium phosphate pH 7.4) was added to wells A1-H10 of the plate ("4153"). To another different, 96-well microtiter plate, 25 µl of diluted PBI 4146 (25 µl 1 mg/ml solution of PBI 4146 with 5 ml of 10 mM potassium phosphate pH 7.4) was added to wells A1-H10 of the plate ("4146"). 25 µl of the diluted enzyme solutions were then added.

Based on previous work with luciferin derivatives, it was not expected that free, reduced glutathione would be able to react with the Coumarin derivatives to release a fluorescent Coumarin species unless GST is present to catalyze the reaction. Thus, no significant change in fluorescence was expected in samples which did not contain GST. If one or more of the GST enzyme forms can catalyze the Coumarin compound in the presence of glutathione, the samples containing a GST enzyme form will have an increase in fluorescence. The better the GST enzyme form can utilize the Coumarin derivative, the more rapid the increase in fluorescence, and the lower the concentrations of GST enzyme needed to be able to produce a substantial increase in fluorescence over time.

Results

Figure 6:
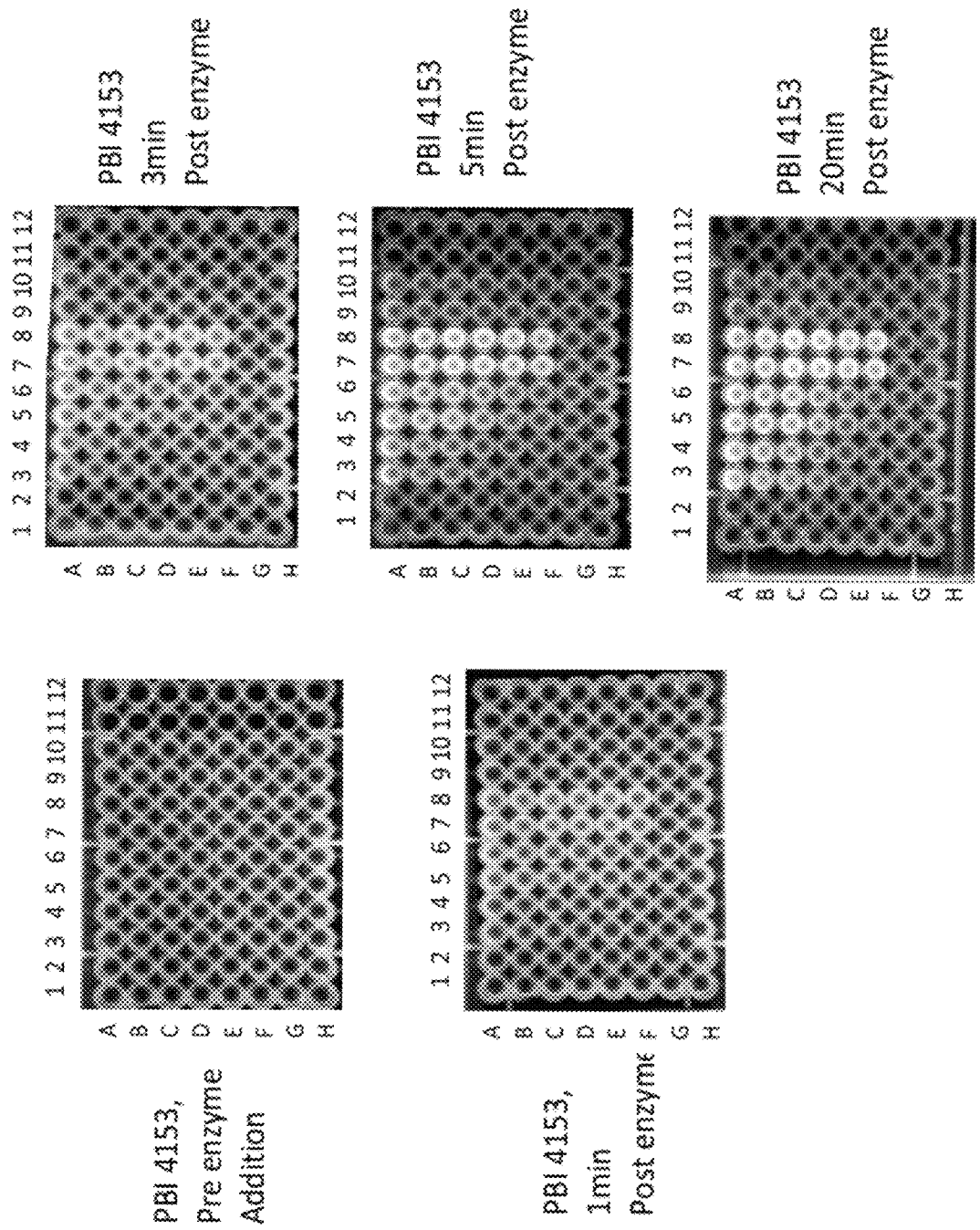
FIG. 6 shows fluorescent detection using coumarin derivatives.

FIG. 6 shows images of plate "4153" at 1, 3, 5, and 20 minute post GST enzyme addition. There is no apparent increase in fluorescence in samples having only buffer ("control wells") confirming that the mere presence of reduced glutathione with the Coumarin derivative does not produce a fluorescent species. However, a relatively rapid increase in fluorescence is seen in samples containing decreasing amounts of GST M with a slower rate of increase in samples containing decreasing amounts of GST A, and an even slower rate of increase in samples containing GST. These results indicate that GST M can rapidly utilize the Coumarin compound as a substrate to generate a fluorescent Coumarin derivative. GST A can also utilize the compound, but at a slower rate. GST from Promega (V689B) also utilized the compound but at an even slower rate than GST A. GST P either did not utilize this compound or utilized it at a very, very slow rate as no increase in fluorescence was seen in the wells containing this enzyme form.

Figure 7:
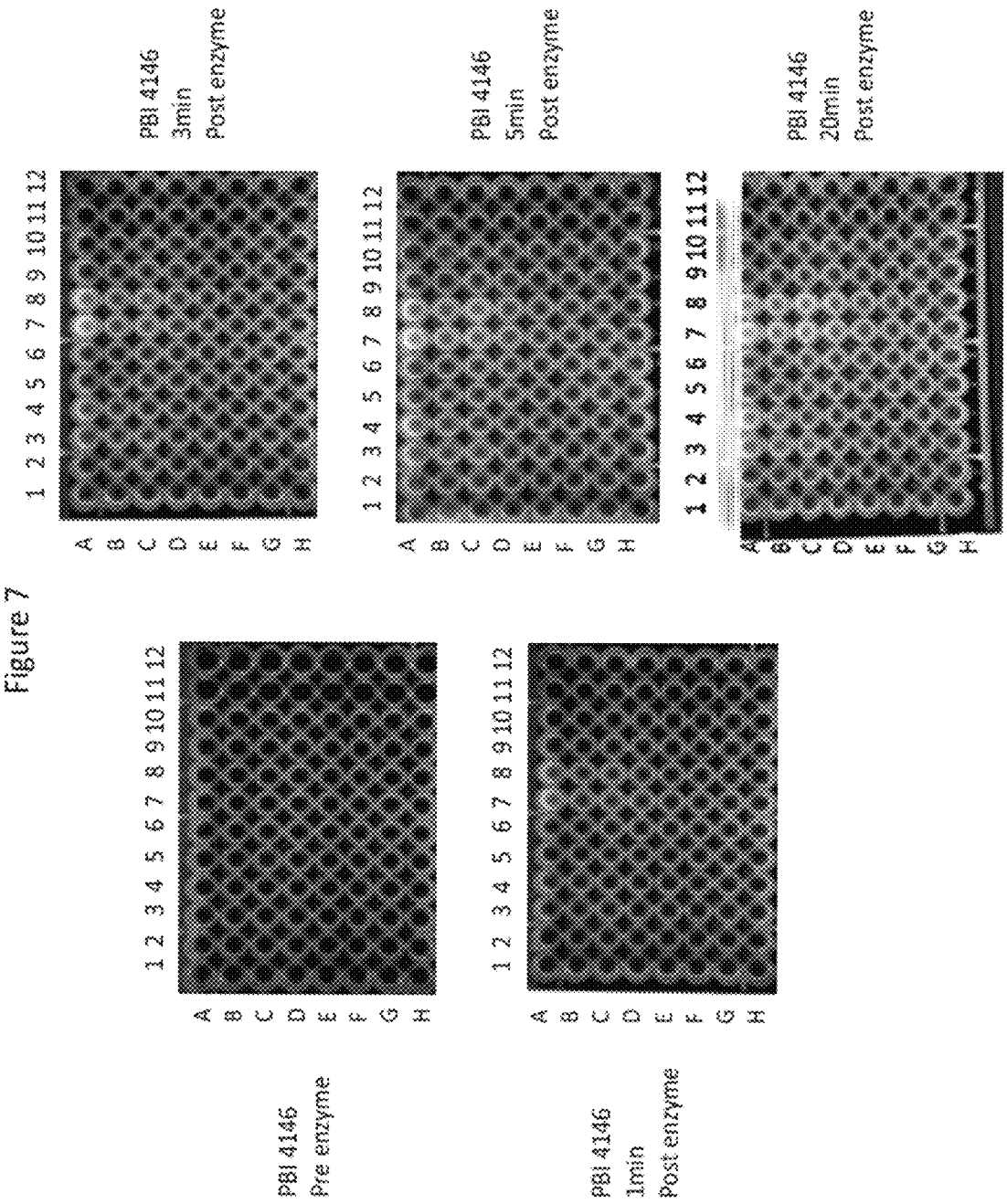
FIG. 7 shows fluorescent detection using coumarin derivatives.
Figure 8:
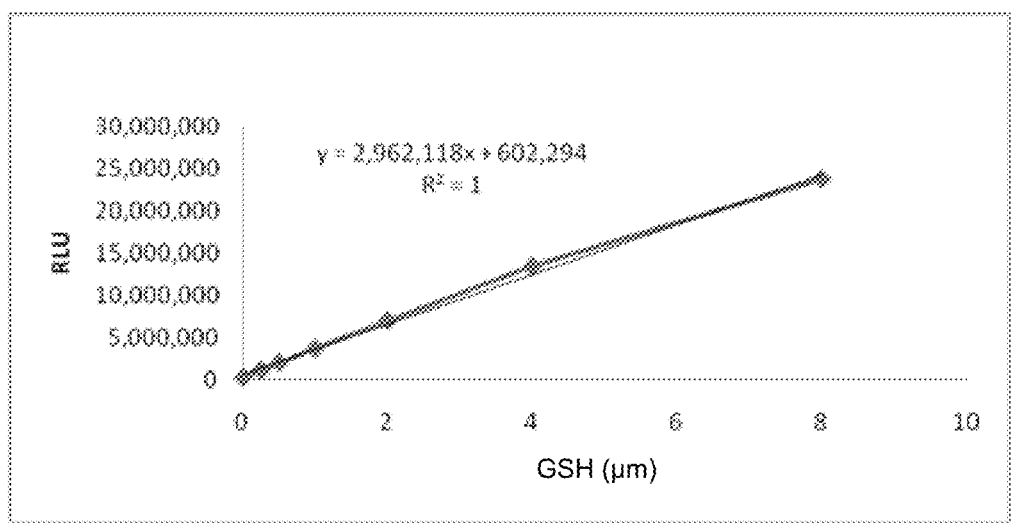
FIG. 8 shows a standard curve for GSH.

FIG. 7 shows images of plate "4146" at 1, 3, 5 and 20 min post GST addition. There is no apparent increase in fluorescence in the wells containing only buffer ("control wells" A1-F2) confirming that the mere presence of reduced glutathione with the Coumarin derivative does not produce a fluorescent species. An increase in fluorescence was seen in wells A7-F8 with a slower rate of increase in A3-F4. These results indicate that GST M can rapidly utilize the Coumarin compound to generate a fluorescent Coumarin derivative. The GST form from Promega can also utilize the compound, but at an even slower rate than GST M. GST A and GST P either did not utilize this compound or utilized it at very, very slow rate as no increase in fluorescence was seen in wells containing these enzyme forms.

These results demonstrate that various GST forms can utilize pre-fluorescent Coumarin derivatives in combination with low concentrations of reduced glutathione to generate a fluorescent signal. Not unexpectedly, some of the GST forms utilize some of the compounds better than other forms, and thus would be preferred for measuring reduced glutathione solely or as generated from oxidized glutathione as in the method of the invention.

Example 28. Determination of GSH:GSSG Ratio

The method of the present invention is designed to measure the ratio of reduced glutathione (GSH) to oxidized glutathione (GSSG) and/or GSSG only in adherent and suspension mammalian cells. Section B describes how the ratio is calculated by dividing the moles of GSH in a sample by the moles of GSSG.

A. Determination of GSSG and GSH Levels
  i. Plating Adherent Cells
The assay is optimized for low cell densities such as HeLa or HepG2 cells at 5,000-10,000 cells per well and hepatocytes at 10,000 to 20,000 cells/well. HeLa or HepG2 cells were plated on Corning Costar 3903 96-well flat bottom tissue culture-treated white with clear bottom. Hepatocytes were plated on BD BioCoat™ 4650 96-well Collagen 1 Cellware. Hepatocytes were cultured with vendor recommended hepatocyte media. If clear walled tissue culture plates are used, a transfer step must be performed after Luciferase Detection Reagent (LDR) addition to get the reactions into luminometer plates. Plate cells and incubate overnight at 37° C. in a 5% $CO_2$ culture incubator.

ii. Treating Adherent Cells

Menadione is a Reactive Oxygen Species (ROS) inducer and is used as a positive control. 40 µM Menadione was prepared in Krebs-Ringer, Krebs-Henseleit, or Hank's Balanced Salts (HBSS) buffers. Other buffers can be used to dilute the Menadione as components of cell culture media, such as serum, phenol red, and cysteine, can interfere with the assay chemistry. No treatment controls (vehicle only) were performed by exchanging the culture media on the cells with buffer+vehicle at the same time as treating the cells with Menadione.

iii. Plating and Treatment Suspension Cells

Suspension cells, such as Jurkat or Hela cells, are washed in Krebs-Ringer, Krebs-Henseleit, or Hank's Balanced Salts (HBSS) buffers to remove traces of medium and serum. Cells are then counted and diluted in one of the above buffers at the desired density. For Jurkat cells, 10,000 to 20,000 cells/well were used. 20 µl of cell suspension (at the desired density) were then added to wells of a 96-well plate. Enough wells with cells were plated for test compound treatment, vehicle-only treatment and no treatment controls. 5 µl of test compound, e.g. menadione, at 5× concentration was then added to the test compound treated cells, and 5 µl of vehicle-only, e.g. DMSO, added to the vehicle-only treated cells. Cells were then incubated at 37° C. in a 5% $CO_2$ incubator for 60 minutes.

iv. Oxidized Glutathione Reagent for GSSG Reactions

The below reagent was prepared for measurement of GSSG. The solution contains 250 µM N-ethylmaleimide (NEM) to block GSH and a pro-luciferin substrate, GST-22, in a cell lysis solution. Each well of a 96-well plate requires 50 µl.

| Oxidized Glutathione Reagent | |
|---|---|
| Component | Volume per 50 µl |
| GST-22 | 1.0 µl |
| 25 mM NEM | 0.5 µl |
| 5X Passive Lysis Buffer (Promega Corporation; Cat. No. E1941) | 10.0 µl |
| Water | 38.5 µl |
| Final volume | 50 µl | iv. Total Glutathione Reagent for GSH Reactions and GSH Standard Curve

The below reagent was prepared for the measurement GSH. The GSH solution does not contain NEM. Each well of a 96-well plate requires 50 µl.

| Total Glutathione Reagent | |
|---|---|
| Component | Volume per 50 µl |
| GST-22 | 1.0 µl |
| 25 mM NEM | 0 |
| 5X Passive Lysis Buffer | 10.0 µl |
| water | 39.0 µl |
| Final volume | 50 µl | v. Luciferin Generation Reagent for all Reactions

The Luciferin Generation Reagent contains DTT and Glutathione-S-Transferase (Promega) diluted in GSH-Glo buffer (Promega; Cat. No. V6911). The reagent was added to all assay wells. Each well of a 96-well plate requires 50 µl.

| Luciferin Generation Reagent | |
|---|---|
| Component | Volume per 50 µl |
| 100 mM DTT | 1.25 µl |
| Glutathione S-Transferase | 3.0 µl |
| GSH-Glo Reaction Buffer | 45.75 µl |
| Final volume | 50 µl | vi. Luciferin Detection Reagent (LDR)

Luciferin Detection Reagent was prepared by reconstituting lyophilized Luciferin Detection Reagent (Promega; Cat. No. V859B) with one bottle of Reconstitution Buffer containing esterase (Promega; Cat. No. V144A). Each well of a 96-well assay will get 100 µl of LDR.

vii. GSH Standard Curve, 0-16 µM

Inclusion of a GSH standard curve allows the correlation of luminescence (in relative light units or RLUs) generation to GSH and GSSG concentration. 20× concentrations of glutathione were prepared by diluting 5 mM Glutathione to 320 µM in water. For example, 32 µl 5 mM GSH into 468 µl water. Serial dilutions were performed by transferring 250 µA 320 µM GSH into 250 µA water, etc. 5 µl 1/well of each GSH dilution in triplicate were performed. For example, 5 µA of 320 µM GSH corresponds to 16 µM GSH for the standard curve. The GSH standard curve was the same for both adherent and suspension cell assays.

viii. Assay Procedure

Compound treatment was removed and discarded from the adherent cells. For measurement of GSSG, 25 µl/well or 50 µl/well of the Oxidized Glutathione Reagent was added to the suspension or adherent cells, respectively. For measurement of GSH, 25 µl/well or 50 µl/well of the Total Glutathione Reagent was added to the suspension or adherent cells, respectively. For measurement of the GSH standard curve, 50 µl/well of Total Glutathione Reagent was added. The plate was allowed to shake at room temperature for 5 minutes on a plate shaker and 50 µl/well Luciferin Generation Reagent added to all wells. The plate was again allowed to shake briefly and incubated at room temperature for 30 minutes followed by the addition of 100 µl/well Luciferin Detection Reagent. Again, the plated was shook briefly, incubated at room temperature for 10 min, and luminescence read.

B. GSSG:GSH Ratio Calculation

The GSSG:GSH ratio is calculated by dividing the moles of GSH in a sample by the moles of GSSG in a sample. Because each mole of GSSG produces two moles of GSH, and the assay produces a signal from all of the GSH produced by reduction of GSSG, a 2-fold adjustment is required in the number of moles of GSH quantified by the GSH standard curve.

i. Calculating Ratio Using Net RLUs

For background, the luminescence (RLUs) generated from no cell control or 0 µM GSH from the standard curve was used. For treated and untreated cells, the average of the background from all wells was subtracted from the RLUs generated from the treated or untreated cells to generate a Net RLU value. The GSH/GSSG ratio for untreated cells was calculated using the formula:

$$\frac{(\text{Net untreated } GSH\ RLU) - \left[\frac{(\text{Net untreated } GSSG\ RLU)}{2}\right]}{\left[\frac{(\text{Net untreated } GSSG\ RLU)}{2}\right]}$$

The GSH/GSSG ratio for treated cells was calculated using the formula:

$$\frac{(\text{Net treated } GSH\ RLU) - \left[\frac{(\text{Net treated } GSSG\ RLU)}{2}\right]}{\left[\frac{(\text{Net treated } GSSG\ RLU)}{2}\right]}$$

ii. Calculating Ratio Using a GSH Standard Curve

Luminescence (RLUs) vs. Concentration (μM) GSH was plotted. A second plot was generated for determining GSSG concentration where, on the x-axis, GSSG concentrations were generated by dividing the GSH values by two. Note: 2 moles GSH per 1 mole GSSG, dividing the GSH concentrations by two gives the concentration of GSSG. Using the slope (m) generated by the linear portion of each standard curve and the formula (Y−B)/m, the average RLU (not net RLU) values of treated and untreated cells were converted to μM GSSG and GSH. The RLU values from no cell control, i.e., 0 μM GSH, were used as "B" in the formula (Y−B)/m. Therefore, the ratio GSH/GSSG for untreated cells=μM GSH untreated−(μM GSSG untreated×2)/μM GSSG untreated, and the ratio GSH/GSSG for treated cells=μM GSH treated−(μM GSSG treated×2)/μM GSSG treated (FIG. 7).

C. Examples Using the Methods Described in A and B:

i. HeLa cells, 5,000 cells/well, were treated for 60 minutes with 40 uM menadione or 0.1% DMSO (vehicle). GSSG and GSH were detected by the method described in A. The ratio GSH/GSSG was calculated as described in B.

|       | Untreated Net RLU | Ratio | Treated Net RLU | Ratio |
|-------|-------------------|-------|-----------------|-------|
| GSH   | 14989340          | 64    | 12364719        | 2.2   |
| GSSG  | 455295            |       | 5894364         |       | ii: Rat hepatocytes, 20,000 cells/well, were treated as in i. GSSG and GSH were detected by the method described in A. The ratio GSH/GSSG was calculated as described in B.

|       | Untreated Net RLU | Ratio | Treated Net RLU | Ratio |
|-------|-------------------|-------|-----------------|-------|
| GSH   | 13141574          | 20    | 10722488        | 1.1   |
| GSSG  | 1205126           |       | 6900404         |       | iii. HepG2 cells, 5,000 cells/well, were treated as in i. GSSG and GSH were detected by the method described in A. The ratio GSH/GSSG was calculated as described in B.

|       | Untreated Net RLU | Ratio | Treated Net RLU | Ratio |
|-------|-------------------|-------|-----------------|-------|
| GSH   | 6850038           | 73    | 4162074         | 1.5   |
| GSSG  | 182161            |       | 2364652         |       | iv. Jurkat cells, 10,000 cells/well or 20,000 cells/well, were treated as in i. GSSG and GSH were detected by the method described in A. The ratio GSH/GSSG was calculated as described in B.

|              | Ratio-Untreated | Ratio-Treated |
|--------------|-----------------|---------------|
| 10,000 cells | 15              | 3.8           |
| 20,000 cells | 22.6            | 3.6           |

Example 29. Purification of GSH-free GST (*S. Japonica*) Enzyme

Reagents

Cell Resuspension Buffer: PBS, 10 mM DTT, 2.5 mM PMSF

Column Wash and Equilibration Buffer: PBS, 10 mM DTT

10× Buffer A: 200 mM sodium phosphate, monobasic, pH 4.0, 5 M NaCl

1× Buffer A: 20 mM sodium phosphate, monobasic, pH 4.0, 500 mM NaCl

Elution Buffer: 20 mM sodium phosphate, monobasic, pH 4.0, 500 mM NaCl, 8 M Urea TEDG buffer: 1×TE, 1 mM DTT, 10% glycerol Storage buffer: 1×PBS, 50% glycerol Cell Resuspension 100 g of cell paste (*E. coli* expressing *S. Japonica* GST enzyme) was resuspended in 600 mls of Cell Resuspension Buffer (6 ml buffer/g cell paste). The solution was mixed until the cell suspension was uniform, and the solution then placed on ice.

Cell Disruption

The resuspended cells were disrupted by passing the cell suspension through a Manten Gaulin twice at 9000 psi, and the lysate collected in a stainless steel bucket placed in an ice-salt bath. After the second pass, the Manton Gaulin was washed with 100-200 mls of Cell Resuspension Buffer and combined with the lysate. The lysate was then centrifuged at 16,000×g for 60 minutes at 4° C.

Column Purification

A purification column was prepared using GST affinity resin comprising reduced glutathione and Sepharose CL-4B gel filtration media (Sigma). The column was packed with 147 mls of GST affinity resin for a ratio of resin to cell paste of 2 ml resin/g cell paste.

The column was equilibrated with 1000 mls of Column Wash and Equilibration Buffer at a flow rate of 9 ml/minute (27.5 cm/hour). The column was then loaded with 1100 ml of lysate and allowed to flow at a rate of 9 ml/minute (27.5 cm/hour). The column was then washed with 1500 ml of Column Wash and Equilibration Buffer at a flow rate of 9 ml/minute (27.5 cm/hour).

The purified GST was eluted from the column using a linear gradient elution of 1× Buffer A (low salt buffer) to Elution Buffer (high salt buffer). First, 375 ml of 1× Buffer A was added to the column for a conductivity of 0.47 ms/cm. Then, 375 mls of Elution Buffer was added for a conductivity of 0.6 6 ms/cm. The flow rate for each elution was 15 ml/minute (45.9 cm/hour). Fifty-one, 20 ml gradient fractions were collected using a fraction collector at a rate of 1.3 min/fraction. After each gradient run, a wash with 750 ml (5 column volumes) of Elution Buffer followed by 1500 ml (10 column volumes) of Column Wash and Equilibration Buffer was performed.

To determine the GST concentration in each fraction, 4 ul of each fraction was mixed with 1 ml Coomassie Plus Protein Assay Reagent (Pierce), and protein concentration determined according to the manufacturer's instructions.

Fractions were then pooled to create GST enzyme solutions having a final concentration of 4 mg/ml.

Dialysis

Each pooled GST enzyme solution was first dialysized twice each in 20 L TEDG buffer (10-20 pool volumes) at 4° C. for 2.5 hours. A final dialysis was performed twice each in 10 L Storage buffer (10 pool volumes) with the first performed at 4° C. for 25 hours and the second performed at 4° C. for 15 hours. Each dialysized fraction was then adjusted to a concentration of 4 mg/ml in Storage Buffer, and the enzyme solution stored at 4° C. until use.

Example 30. Detection of Reactive Oxygen Effects by Sampling Media

In this example, a method is provided to monitor cell health after treatment with a compound(s) or chemical(s) that may affect production of reactive oxygen species in the cell. Various researchers have identified that mammalian cells express a transporter that exports oxidized glutathione (GSSG) from the cell (Minich, T. et. al., J. Neurochem. 2006, vol 97, p 373-384). The export of GSSG should relate to the level of GSSG present in the cell, and, therefore, the export of the compound(s) or chemical(s) would be in competition with regeneration of GSH from GSSG in the cell from enzymes such as glutathione reductase. Thus, it may be possible to detect increases in GSSG level in cells by measuring an increase in extracellular GSSG.

For such a measurement to be performed, it is advantageous that the cell media used when treating the cells not contain glutathione, and that serum not be added as many sources of media and serum contain substantial levels of glutathione. If cell media, such as DMEM with fetal calf serum, is used, the starting levels of glutathione in the media will make measurement of exported glutathione more difficult. For this reason, Hank's buffered salt solution (HBSS) was chosen as the media in this example.

A549 cells were plated at a density of 5,000 cells per well in a 96-well tissue culture plate in 100 ul of DMEM with 10% fetal calf serum and incubated for 48 hours at 37° C. with 10% $CO_2$. After incubation, the media was removed, discarded, and replaced with HBSS buffer with or without 40 uM menadione. The plate was then incubated for 1 hour at 37° C. with 10% $CO_2$.

After the 1 hour treatment, the HBSS buffer from the cells was transferred to a fresh, 96-well plate. The cells were then given 100 ul of fresh HBSS buffer and a concentrated solution of PLB with or without NEM. The following conditions (in triplicate) resulted from these manipulations:

1. Cell GSH and GSSG were measured from the lysate of cells where the vehicle or menadione treatment with HBSS buffer was removed prior to lysis.
2. Media GSH and GSSG were measure from the HBSS buffer transferred from the cells.
3. Total GSH and total GSSG were measured from the lysate of cells treated with HBSS buffer where the HBSS buffer was not removed prior to addition of PLB.

For measurement of GSSG, samples were given a mixture containing GST-22, 25 mM NEM, and 1× Passive Lysis Buffer. For measurement of GSH, samples were given a mixture containing GST-22 and 1× Passive Lysis Buffer. Samples were incubated for 5 minutes at room temperature, and 25 µl LDR with 100 mM DTT and GST added. Samples were then incubated for 30 minutes at room temperature, and 150 µl LDR added. Luminescence was detected after 15 minute room temperature incubation.

Figure 9:
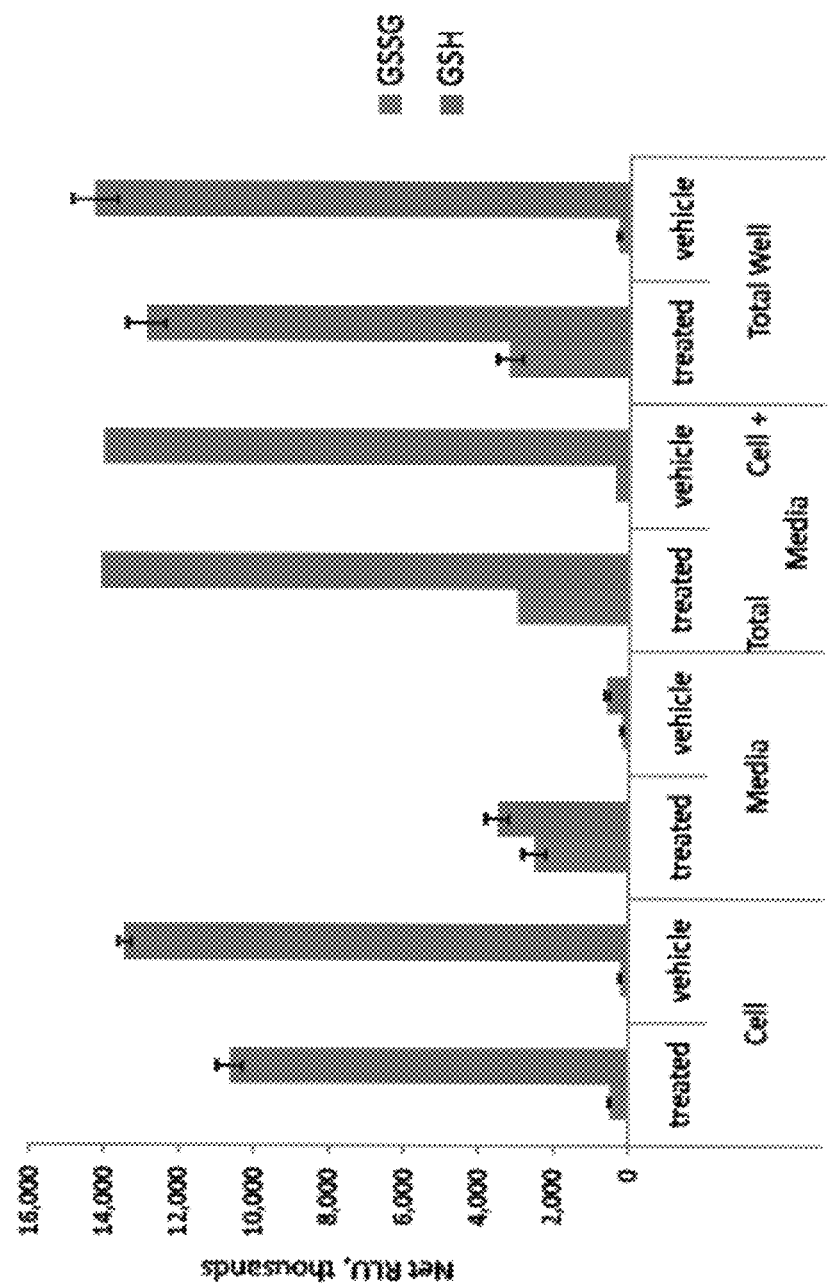
FIG. 9 shows the average RLUs for cell GSH and GSSG, media GSH and GSSH and total GSH and GSSG.
Figure 10:
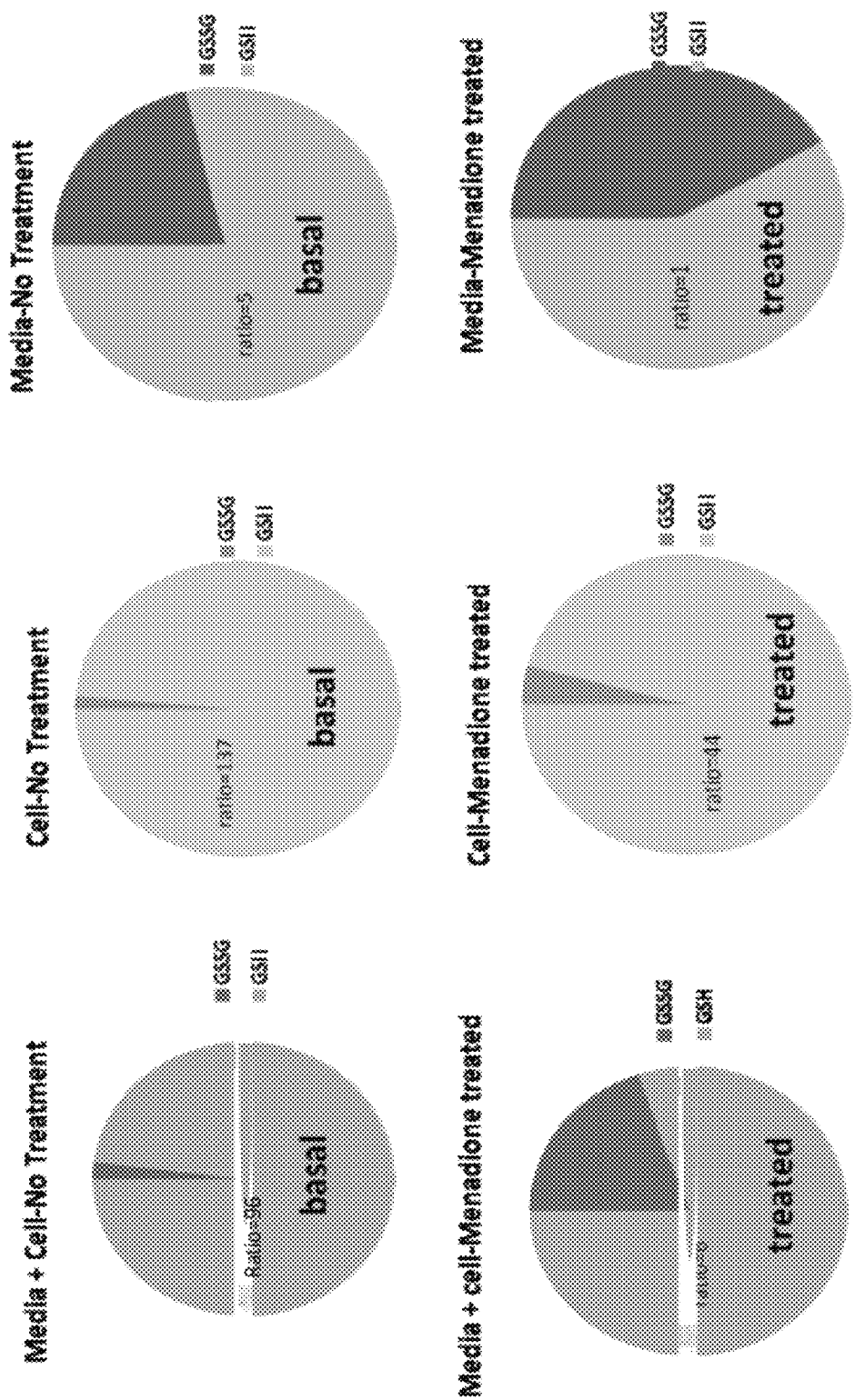
FIG. 10 shows the ratio of GSH to GSSG in cells and media.

The averaged RLU readings from the three conditions are shown in the Table 7 and FIG. 9. It should be noted that one could expect the total glutathione species from the media and the cells to be about equal to the total well measurement. This calculation is shown in the third row of Table 7. The ratio of GSH to GSSG was also determined (FIG. 10).

TABLE 7

|  |  | GSSG | Std. Dev. | GSH | Std. Dev. |
|---|---|---|---|---|---|
| Cell | Menadione | 464,099 | 46,008 | 10,613,488 | 366,115 |
|  | vehicle | 193,425 | 40,854 | 13,430,507 | 197,686 |
| Media | Menadione | 2,494,444 | 329,334 | 3,491,077 | 323,039 |
|  | vehicle | 156,486 | 49,012 | 581,157 | 68,092 |
| Total (Cell + Media) | Menadione | 2,958,543 |  | 14,104,565 |  |
|  | vehicle | 349,911 |  | 14,011,664 |  |
| Total Well | Menadione | 3,189,598 | 344,467 | 12,903,498 | 527,784 |
|  | vehicle | 293,087 | 49,467 | 14,307,800 | 614,533 |

From the data in Table 7 and FIG. 9, it is clear that measurement of GSSG in the media alone would have indicated some effect of the menadione treatment on the cells. While lysis of a fraction of the cells might also raise the media values for GSSG dramatically, in this case measurements of cell lysis (LDH release and ATP levels) did not suggest that any lysis had taken place (data not shown).

Therefore, this data indicates that measurement of GSSG and GSH in cell media using the method of the present invention can be used to detect the effect of a compound(s) on cell health. Since cell media is typically removed and disgarded in many experiments, use of the cell media as a measure of cell health could be done without sacrificing any cells or cell lysate allowing other assays, e.g., cell viability or enzymatic assays, to be performed on the cells as well to allow for more information to be obtained from a single sample.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The invention claimed is:

1. A method for detecting GSSG comprising:
    a. contacting a sample with a sulfhydryl alkylating agent;
    b. contacting the sample with an excess of a reducing agent, glutathione-S-transferase, and a substrate for glutathione-S-transferase which is converted to a signal-generating compound in the presence of GSH and glutathione-S-transferase, wherein the reducing agent inactivates the sulfhydryl alkylating agent and reduces any GSSG in the sample to GSH; and
    c. detecting the signal generated from step (b), thereby confirming the presence of GSSG in the sample, wherein neither the inactivated sulfhydryl alkylating agent nor the reducing agent is removed from the sample.

2. The method of claim 1 wherein the signal is quantified.

3. The method of claim 1 wherein the sample comprises a cell, media, plasma, serum, blood, or tissue extract.

4. The method of claim 1 further comprising contacting the sample with a lysing agent in step a.

5. The method of claim 1 wherein the signal is luminescence.

6. The method of claim 1 wherein the substrate for glutathione-S-transferase is a luciferin derivative which is converted to luciferin in the presence of GSH and glutathione-S-transferase.

7. The method of claim 1 wherein the substrate is a compound of formula (III)

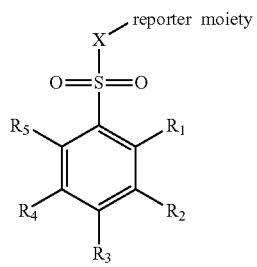

(III)

wherein X is NO or O;

wherein $R_1$, $R_2$, $R_3$, $R_4$ and $R_5$ are independently H, $C_{1-6}$ alkyl, $CF_3$, halogen, $NO_2$, $CO_2R$, wherein R is H or $C_{1-6}$ alkyl, or any two adjacent $R_1$-$R_5$ can form a fused ring provided that at least one of $R_1$, $R_3$ or $R_5$ is $NO_2$ and not all three are $NO_2$.

8. The method of claim 7 wherein the fused ring is benzo, naphtho, or hetrocyclic.

9. The method of claim 1 wherein the sulfhydryl modifying agent is N-ethylmaleimide.

10. The method of claim 1 wherein the reducing agent is DTT.

11. A method of determining oxidative stress in a sample comprising:
   (a) contacting the sample with a sulfhydryl alkylating agent;
   (b) contacting the sample with an excess of a reducing agent, glutathione-S-transferase, and a substrate for glutathione-S-transferase which is converted to a signal-generating compound in the presence of GSH and glutathione-S-transferase, wherein the reducing agent inactivates the sulfhydryl alkylating agent and reduces any GSSG in the sample to GSH; and
   (c) measuring the signal, thereby confirming oxidative stress in the sample, wherein neither the inactivated sulfhydryl alkylating agent nor the reducing agent is removed from the sample.

12. The method of claim 11 wherein the sample comprises a cell, media, plasma, serum, blood, or tissue extract.

13. The method of claim 11 further comprising contacting the sample with a lysing agent in step a.

14. The method of claim 11 wherein the signal is luminescence.

15. The method of claim 11 wherein the substrate for glutathione-S-transferase is a luciferin derivative which is converted to luciferin in the presence of GSH and glutathione-S-transferase.

16. The method of claim 11 wherein the substrate is a compound of formula (III)

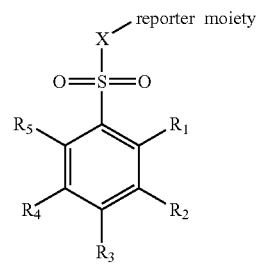

(III)

wherein X is N or O;

wherein $R_1$, $R_2$, $R_3$, $R_4$ and $R_5$ are independently H, $C_{1-6}$ alkyl, $CF_3$, halogen, $NO_2$, $CO_2R$, wherein R is H or $C_{1-6}$ alkyl, or any two adjacent $R_1$-$R_5$ can form a fused ring provided that at least one of $R_1$, $R_3$ or $R_5$ is $NO_2$ and not all three are $NO_2$.

17. The method of claim 16 wherein the fused ring is benzo, naphtho, or hetrocyclic.

18. The method of claim 11 wherein the sulfhydryl modifying agent is N-ethylmaleimide.

19. The method of claim 11 wherein the reducing agent is DTT.

20. A method for detecting GSSG comprising:
   a. contacting a sample with a sulfhydryl alkylating agent;
   b. contacting the sample with an excess of a reducing agent, glutathione-S-transferase, and a substrate for glutathione-S-transferase which is converted to a signal-generating compound in the presence of GSH and glutathione-S-transferase, wherein the reducing agent inactivates the sulfhydryl alkylating agent and reduces any GSSG in the sample to GSH; and
   c. detecting the signal generated from step (b), thereby confirming the presence of GSSG in the sample, wherein neither the inactivated sulfhydryl alkylating agent nor the reducing agent is removed from the sample, and wherein the signal is fluorescence.

21. The method of claim 20 wherein the signal is quantified.

22. The method of claim 20 wherein the sample comprises a cell, media, plasma, serum, blood, or tissue extract.

23. The method of claim 20 further comprising contacting the sample with a lysing agent in step a.

24. The method of claim 20 wherein the sulfhydryl modifying agent is N-ethylmaleimide.

25. The method of claim 20 wherein the reducing agent is DTT.

26. A method of determining oxidative stress in a sample comprising:
   (a) contacting the sample with a sulfhydryl alkylating agent;
   (b) contacting the sample with an excess of a reducing agent, glutathione-S-transferase, and a substrate for glutathione-S-transferase which is converted to a signal-generating compound in the presence of GSH and glutathione-S-transferase, wherein the reducing agent inactivates the sulfhydryl alkylating agent and reduces any GSSG in the sample to GSH; and
   (c) measuring the signal, thereby confirming oxidative stress in the sample, wherein neither the inactivated sulfhydryl alkylating agent nor the reducing agent is removed from the sample, and wherein the signal is fluorescence.

27. The method of claim 26 wherein the signal is quantified.

28. The method of claim 26 wherein the sample comprises a cell, media, plasma, serum, blood, or tissue extract.

29. The method of claim 26 further comprising contacting the sample with a lysing agent in step a.

30. The method of claim 26 wherein the sulfhydryl modifying agent is N-ethylmaleimide.

31. The method of claim 26 wherein the reducing agent is DTT.

* * * * *